US007235232B2

(12) United States Patent
Zoon et al.

(10) Patent No.: US 7,235,232 B2
(45) Date of Patent: Jun. 26, 2007

(54) INTERFERON ALPHA HYBRIDS

(75) Inventors: Kathryn C. Zoon, Kensington, MD (US); Renqiu Hu, Bethesda, MD (US); Joseph B. Bekisz, Hyattsville, MD (US); Mark P. Hayes, Westborough, MA (US)

(73) Assignee: The Government of the United States of America as represented by the Secretary of the Department of Health and Human Services, Washington, DC (US)

( * ) Notice: Subject to any disclaimer, the term of this patent is extended or adjusted under 35 U.S.C. 154(b) by 589 days.

(21) Appl. No.: 10/615,723

(22) Filed: Jul. 8, 2003

(65) Prior Publication Data

US 2004/0018172 A1 Jan. 29, 2004

Related U.S. Application Data

(62) Division of application No. 09/744,754, filed as application No. PCT/US99/15284 on Jul. 6, 1999, now Pat. No. 6,685,933.

(60) Provisional application No. 60/094,407, filed on Jul. 28, 1998.

(51) Int. Cl.
*A61K 38/21* (2006.01)
*A61K 39/00* (2006.01)
*C07K 14/00* (2006.01)
*C12P 21/00* (2006.01)
*C12N 15/21* (2006.01)

(52) U.S. Cl. .................. 424/85.4; 424/185.1; 530/350; 530/351; 435/69.51; 435/69.1; 435/252.3

(58) Field of Classification Search ..................... None
See application file for complete search history.

(56) References Cited

U.S. PATENT DOCUMENTS

| | | | |
|---|---|---|---|
| 4,569,908 A | 2/1986 | Mark | |
| 4,716,217 A | 12/1987 | Caruthers | |
| 4,758,428 A | 7/1988 | Mark | |
| 4,806,347 A | 2/1989 | Leibowitz | |
| 4,820,638 A | 4/1989 | Swetly | |
| 4,885,166 A | 12/1989 | Meyer | |
| 4,892,743 A | 1/1990 | Leibowitz | |
| 4,914,033 A | 4/1990 | Bell | |
| 4,917,887 A | 4/1990 | Hauptmann | |
| 5,071,761 A | 12/1991 | Meyer | |
| 5,089,400 A | 2/1992 | Meyer | |
| 5,593,667 A | 1/1997 | Kung | |
| 5,609,868 A | 3/1997 | Lowther | |

FOREIGN PATENT DOCUMENTS

EP 0626448 A 11/1994

OTHER PUBLICATIONS

Alexanko et al., "Mapping of an epitope of human leukocyte alpha interferon A which is recognized by the murine monoclonal antibody NK2," *Biomed. Sci.*, 2(4):403-409, 1991.

Alexanko et al., "Recontruction of an epitope cabaple of binding murine monoclonal antibodies NK2 within the sequence of human leukocyte interferon alpha F by site-directed mutagenesis," *Biochem. Biophys. Res. Commun.*, 169(3):1061-1067, Jun. 29, 1990.

Allen et al., "Nomenclature of the Human Interferon Proteins," *J. Interferon Cytokine Res.*, 16:181-184, 1996.

Di Marco et al., "Mutational analysis of the structure-function relationship in interferon-alpha," *Biochem. Biophys. Res. Comm.*, 202(3):1445-1451, Aug. 1994.

Fidler et al., "Direct antiproliferative effects of recombinant human interferon-alpha B/D hybrids on human tumor cell lines," *Cancer Res.*, 47(8):2020-2027, Apr. 15, 1987.

Fish et al., "Human leukocyte interferon subtypes have different antiproliferative and antiviral activities on human cells," *Biochem. Biophys. Res. Commun.*, 112(2):537-546, Apr. 29, 1983.

Goeddel et al., "The structure of eight distinct cloned human leukocyte interferon cDNAs," *Nature, GB, Macmillan Journals Ltd. London*, 290:20-26, Mar. 5, 1981.

Horisberger and Di Marco, "Interferon-alpha hybrids," *Pharmac. Ther.* 66(3):507-534, 1995.

Hu et al, "Divergence of Binding, Signaling, and Biological Responses to Recombinant Human Hybrid IFN," *J. Immunol.*, 16(2):854-860, Jul. 15, 1999.

Horton et al., "Engineering hybrid genes without the use of restriction enzymes: gene splicing by overlap extension," *Gene, NL, Elservier Biomedical Press, Amsterdam*, 77:61-68, 1989.

Hu et al., "HuIFNalpha21 gene expression and properties of recombinant IFNalpha21," *J. Interferon Res.*, 14(suppl1):S98, Sep. 1994.

Meister et al., "Biological activities and receptor binding of two human recombinant interferons and their hybrids," *J. Gen. Virol.*, 67(8):1633-1643, Aug. 1986.

Rehberg et al., "Specific molecular activities of recombinant and hybrid leukocyte interferons," *J. Biol. Chem.*, 257(19):11497-11502, Oct. 10, 1982.

Sperber et al., "Anti-rhonoviral activity of recombinant and hybrid species of interferon alpha," *Antiviral Res.*, 22(2-3):121-129, Oct. 1993.

Streuli et al., "Target cell specificity of two species of human interferon-alpha produced in *Escherichia coli* and hybrid molecules drived from them," *Proc. Natl. Acad. Sci. USA*, 78(5):2848-2852, May 1981.

Weck et al., "Antiviral activities of hybrids of two major human leukocyte interferons," *Nucleic acids. Res.*, 9(22):6153-6156, Nov. 25, 1981.

*Primary Examiner*—Christine J. Saoud
*Assistant Examiner*—Jegatheesan Seharaseyon
(74) *Attorney, Agent, or Firm*—Klarquist Sparkman LLP

(57) ABSTRACT

Hybrid human interferon-α polypeptides, and the corresponding nucleic acid molecules, are disclosed. Pharmaceutical compositions comprising these peptides, and the use of these polypeptides to treat viral disease and regulate cell growth are also provided.

23 Claims, 10 Drawing Sheets

PCR#1

Reaction #1           Reaction #2

IFN-α 21b Gene           IFN-α 2c Gene

↓ PCR Amplification

α 21b DNA Fragments           α 2c DNA Fragments

PCR#2

Reaction #1 and #2 Fragments

↓

IFN-α21b   75   IFN-α2c      HY1
(IFN-α Hybrid 1)

Construction of Hybrid #1

PCR#1

Reaction #1

IFN-α 21b Gene

Reaction #2

IFN-α 2c Gene

↓ PCR Amplification

```
_____95_____            95_____
```

α 21b DNA Fragments            α 2c DNA Fragments

PCR#2

Construction of Hybrid #2

PCR#1

Reaction #1

IFN-α 2c Gene

Reaction #2

IFN-α 21b Gene

↓ PCR Amplification

Construction of Hybrid #3

|          | 1 | 2 | 3 | 4 | 5 | 6 | 7 | 8 | 9 | 10 | 11 | 12 | 13 | 14 | 15 | 16 | 17 |
|----------|---|---|---|---|---|---|---|---|---|----|----|----|----|----|----|----|----|
| Alpha 2c | C | D | L | P | Q | T | H | S | L | G  | S  | R  | R  | T  | L  | M  | L  |
| Alpha 21b| C | D | L | P | Q | T | H | S | L | G  | N  | R  | R  | A  | L  | I  | L  |
| HY-1     | C | D | L | P | Q | T | H | S | L | G  | N  | R  | R  | A  | L  | I  | L  |
| HY-2     | C | D | L | P | Q | T | H | S | L | G  | N  | R  | R  | A  | L  | I  | L  |
| HY-3     | C | D | L | P | Q | T | H | S | L | G  | S  | R  | R  | T  | L  | M  | L  |

|          | 18 | 19 | 20 | 21 | 22 | 23 | 24 | 25 | 26 | 27 | 28 | 29 | 30 | 31 | 32 | 33 | 34 |
|----------|----|----|----|----|----|----|----|----|----|----|----|----|----|----|----|----|----|
| Alpha 2c | L  | A  | Q  | M  | R  | R  | I  | S  | L  | F  | S  | C  | L  | K  | D  | R  | R  |
| Alpha 21b| L  | A  | Q  | M  | G  | R  | I  | S  | P  | F  | S  | C  | L  | K  | D  | R  | H  |
| HY-1     | L  | A  | Q  | M  | G  | R  | I  | S  | P  | F  | S  | C  | L  | K  | D  | R  | H  |
| HY-2     | L  | A  | Q  | M  | G  | R  | I  | S  | P  | F  | S  | C  | L  | K  | D  | R  | H  |
| HY-3     | L  | A  | Q  | M  | R  | R  | I  | S  | L  | F  | S  | C  | L  | K  | D  | R  | R  |

|          | 35 | 36 | 37 | 38 | 39 | 40 | 41 | 42 | 43 | 44 | 45 | 46 | 47 | 48 | 49 | 50 | 51 |
|----------|----|----|----|----|----|----|----|----|----|----|----|----|----|----|----|----|----|
| Alpha 2c | D  | F  | G  | F  | P  | Q  | E  | E  | F  | *  | G  | N  | Q  | F  | Q  | K  | A  |
| Alpha 21b| D  | F  | G  | F  | P  | Q  | E  | E  | F  | D  | G  | N  | Q  | F  | Q  | K  | A  |
| HY-1     | D  | F  | G  | F  | P  | Q  | E  | E  | F  | D  | G  | N  | Q  | F  | Q  | K  | A  |
| HY-2     | D  | F  | G  | F  | P  | Q  | E  | E  | F  | D  | G  | N  | Q  | F  | Q  | K  | A  |
| HY-3     | D  | F  | G  | F  | P  | Q  | E  | E  | F  | *  | G  | N  | Q  | F  | Q  | K  | A  |

|          | 52 | 53 | 54 | 55 | 56 | 57 | 58 | 59 | 60 | 61 | 62 | 63 | 64 | 65 | 66 | 67 | 68 |
|----------|----|----|----|----|----|----|----|----|----|----|----|----|----|----|----|----|----|
| Alpha 2c | E  | T  | I  | P  | V  | L  | H  | E  | M  | I  | Q  | Q  | I  | F  | N  | L  | F  |
| Alpha 21b| Q  | A  | I  | S  | V  | L  | H  | E  | M  | I  | Q  | Q  | T  | F  | N  | L  | F  |
| HY-1     | Q  | A  | I  | S  | V  | L  | H  | E  | M  | I  | Q  | Q  | T  | F  | N  | L  | F  |
| HY-2     | Q  | A  | I  | S  | V  | L  | H  | E  | M  | I  | Q  | Q  | T  | F  | N  | L  | F  |
| HY-3     | E  | T  | I  | P  | V  | L  | H  | E  | M  | I  | Q  | Q  | I  | F  | N  | L  | F  |

|          | 69 | 70 | 71 | 72 | 73 | 74 | 75 | 76 | 77 | 78 | 79 | 80 | 81 | 82 | 83 | 84 | 85 |
|----------|----|----|----|----|----|----|----|----|----|----|----|----|----|----|----|----|----|
| Alpha 2c | S  | T  | K  | D  | S  | S  | A  | A  | W  | D  | E  | T  | L  | L  | D  | K  | F  |
| Alpha 21b| S  | T  | K  | D  | S  | S  | A  | T  | W  | E  | Q  | S  | L  | L  | E  | K  | F  |
| HY-1     | S  | T  | K  | D  | S  | S  | A  | A  | W  | D  | E  | T  | L  | L  | D  | K  | F  |
| HY-2     | S  | T  | K  | D  | S  | S  | A  | T  | W  | E  | Q  | S  | L  | L  | E  | K  | F  |
| HY-3     | S  | T  | K  | D  | S  | S  | A  | A  | W  | D  | E  | T  | L  | L  | D  | K  | F  |

|          | 86 | 87 | 88 | 89 | 90 | 91 | 92 | 93 | 94 | 95 | 96 | 97 | 98 | 99 | 100 | 101 | 102 |
|----------|----|----|----|----|----|----|----|----|----|----|----|----|----|----|-----|-----|-----|
| Alpha 2c | Y  | T  | E  | L  | Y  | Q  | Q  | L  | N  | D  | L  | E  | A  | C  | V   | I   | Q   |
| Alpha 21b| S  | T  | E  | L  | N  | Q  | Q  | L  | N  | D  | L  | E  | A  | C  | V   | I   | Q   |
| HY-1     | Y  | T  | E  | L  | Y  | Q  | Q  | L  | N  | D  | L  | E  | A  | C  | V   | I   | Q   |
| HY-2     | S  | T  | E  | L  | N  | Q  | Q  | L  | N  | D  | L  | E  | A  | C  | V   | I   | Q   |
| HY-3     | Y  | T  | E  | L  | Y  | Q  | Q  | L  | N  | D  | L  | E  | A  | C  | V   | I   | Q   |

|          | 103 | 104 | 105 | 106 | 107 | 108 | 109 | 110 | 111 | 112 | 113 | 114 | 115 | 116 | 117 | 118 | 119 |
|----------|-----|-----|-----|-----|-----|-----|-----|-----|-----|-----|-----|-----|-----|-----|-----|-----|-----|
| Alpha 2c | G   | V   | G   | V   | T   | E   | T   | P   | L   | M   | K   | E   | D   | S   | I   | L   | A   |
| Alpha 21b| E   | V   | G   | V   | E   | E   | T   | P   | L   | M   | N   | V   | D   | S   | I   | L   | A   |
| HY-1     | G   | V   | G   | V   | T   | E   | T   | P   | L   | M   | K   | E   | D   | S   | I   | L   | A   |
| HY-2     | G   | V   | G   | V   | T   | E   | T   | P   | L   | M   | K   | E   | D   | S   | I   | L   | A   |
| HY-3     | E   | V   | G   | V   | E   | E   | T   | P   | L   | M   | N   | V   | D   | S   | I   | L   | A   |

|          | 120 | 121 | 122 | 123 | 124 | 125 | 126 | 127 | 128 | 129 | 130 | 131 | 132 | 133 | 134 | 135 | 136 |
|----------|-----|-----|-----|-----|-----|-----|-----|-----|-----|-----|-----|-----|-----|-----|-----|-----|-----|
| Alpha 2c | V   | R   | K   | Y   | F   | Q   | R   | I   | T   | L   | Y   | L   | K   | E   | K   | K   | Y   |
| Alpha 21b| V   | K   | K   | Y   | F   | Q   | R   | I   | T   | L   | Y   | L   | T   | E   | K   | K   | Y   |
| HY-1     | V   | R   | K   | Y   | F   | Q   | R   | I   | T   | L   | Y   | L   | K   | E   | K   | K   | Y   |
| HY-2     | V   | R   | K   | Y   | F   | Q   | R   | I   | T   | L   | Y   | L   | K   | E   | K   | K   | Y   |
| HY-3     | V   | K   | K   | Y   | F   | Q   | R   | I   | T   | L   | Y   | L   | T   | E   | K   | K   | Y   |

|          | 137 | 138 | 139 | 140 | 141 | 142 | 143 | 144 | 145 | 146 | 147 | 148 | 149 | 150 | 151 | 152 | 153 |
|----------|-----|-----|-----|-----|-----|-----|-----|-----|-----|-----|-----|-----|-----|-----|-----|-----|-----|
| Alpha 2c | S   | P   | C   | A   | W   | E   | V   | V   | R   | A   | E   | I   | M   | R   | S   | F   | S   |
| Alpha 21b| S   | P   | C   | A   | W   | E   | V   | V   | R   | A   | E   | I   | M   | R   | S   | F   | S   |
| HY-1     | S   | P   | C   | A   | W   | E   | V   | V   | R   | A   | E   | I   | M   | R   | S   | F   | S   |
| HY-2     | S   | P   | C   | A   | W   | E   | V   | V   | R   | A   | E   | I   | M   | R   | S   | F   | S   |
| HY-3     | S   | P   | C   | A   | W   | E   | V   | V   | R   | A   | E   | I   | M   | R   | S   | F   | S   |

|          | 154 | 155 | 156 | 157 | 158 | 159 | 160 | 161 | 162 | 163 | 164 | 165 | 166 |
|----------|-----|-----|-----|-----|-----|-----|-----|-----|-----|-----|-----|-----|-----|
| Alpha 2c | L   | S   | T   | N   | L   | Q   | E   | S   | L   | R   | S   | K   | E   |
| Alpha 21b| L   | S   | K   | I   | F   | Q   | E   | R   | L   | R   | R   | K   | E   |
| HY-1     | L   | S   | T   | N   | L   | Q   | E   | S   | L   | R   | S   | K   | E   |
| HY-2     | L   | S   | T   | N   | L   | Q   | E   | S   | L   | R   | S   | K   | E   |
| HY-3     | L   | S   | K   | I   | F   | Q   | E   | R   | L   | R   | R   | K   | E   |

FIG. 5

INTERFERON ALPHA HYBRIDS

CROSS REFERENCE TO RELATED APPLICATIONS

This is divisional of U.S. patent application Ser. No. 09/744,754, filed Jan. 24, 2001, now U.S. Pat. No. 6,685,933, which is a U.S. National Stage of International Application No. PCT/US99/15284, filed Jul. 6, 1999, which was published in English under PCT Article 21 (2), and which claims the benefit of U.S. Provisional Application No. 60/094,407, filed Jul. 28, 1998. Each of the foregoing applications is incorporated herein in their entirely.

FIELD OF THE INVENTION

This invention relates to human interferon-α hybrids and nucleic acid molecules that encode these hybrids.

BACKGROUND OF THE INVENTION

Interferons are cytokines produced by a variety of eukaryotic cells upon exposure to certain environmental stimuli, including mitogens, endotoxins, double stranded RNA, and viral infection. In addition to having antiviral properties, interferons have been shown to affect a wide variety of cellular functions. These effects include inhibition of cell proliferation, immune regulatory functions and activation of multiple cellular genes. Interferons (IFNs) have been classified into four groups according to their chemical, immunological, and biological characteristics: α(leukocyte), β(fibroblast), γ, and ω. IFNs are further identified by the eukaryote in which they originated, with HuIFN indicating human interferon, for instance.

HuIFN-αs are encoded by a multigene family consisting of about 20 genes; each gene encodes a single subtype of the HuIFN-α. Amino acid sequence identity among IFN-αsubtypes is generally 80-85% (Horisberger and Di Marco 1995). HuIFN-α polypeptides are produced by a number of human cell lines and human leukocyte cells after exposure to viruses or double-stranded RNA, or in transformed leukocyte cell lines (e.g., lymphoblastoid lines).

IFN-αs act through interaction with cell-surface receptors and induce the expression, primarily at the transcriptional level, of a broad but specific set of cellular genes. Several IFN-induced gene products have been used as markers for the biological activity of interferons. These include, for instance, ISG15, ISG54, IRF1, GBP, and IP10.

Individual IFN-αsubtypes have different biological activities. For instance, it was recognized early in interferon research that IFN-α1 and IFN-α2 have distinct target-cell specificities. Human IFN-α2 shows high specific activity on bovine and human cells (similar to most HuIFN-αs), whereas human IFN-α1 shows high activity only on bovine cells.

Interferon activities were first characterized in relation to viral infections, and IFN-αs have proven to be remarkably effective antiviral agents. The current definition of IFN activity units is expressed in virological terms. There are many assays known to those skilled in the art that measure the degree of resistance of cells to viruses (McNeill, 1981). These assays generally can be categorized into three types: inhibition of cytopathic effect; virus plaque formation; and reduction of virus yield. Viral cytopathic effect assays measure the degree of protection induced in cell cultures pre-treated with IFN and subsequently infected with viruses. Vesicular stomatitis virus, for instance, is an appropriate virus for use in such an assay. This type of assay is convenient for screening numerous different IFNs, as it can be performed in 96-well plates (Rubinstein et al., 1981). Plaque-reduction assays measure the resistance of IFN-treated cell cultures to a plaque-forming virus (for instance, measles virus). One benefit to this assay is that it allows precise measurement of a 50% reduction in plaque formation. Finally, virus yield assays measure the amount of virus released from cells during, for instance, a single growth cycle. Such assays are useful for testing the antiviral activity of IFNs against viruses that do not cause cytopathic effects, or that do not build plaques in target-cell cultures. The multiplicity of infection (moi) is an important factor to consider when using either plaque-reduction or virus-yield assays.

Other clinically important interferon characteristics are also easily assayed in the laboratory setting. One such characteristic is the ability of an interferon polypeptide to bind to specific cell-surface receptors. For instance, some IFN-αs exhibit different cell-surface properties compared to IFN-α2b, the IFN most widely used in clinical trials. While IFN-α2b is an effective antiviral agent, it causes significant adverse side effects. Interferons that exhibit distinct binding properties from IFN-α2b may not cause the same adverse effects. Therefore, interferons that compete poorly with IFN-α2b for binding sites on cells are of clinical interest. Competitive interferon binding assays are well known in the art (Hu et al., 1993; Di Marco et al., 1994). In general, such assays involve incubation of cell culture cells with a mixture of $^{125}$I-labeled IFN-α2b and an unlabeled interferon of interest. Unbound interferon is then removed, and the amount of bound label (and by extension, bound $^{125}$I-labeled IFN-α2b) is measured. By comparing the amount of label that binds to cells in the presence or absence of competing interferons, relative binding affinities can be calculated.

Another prominent effect of IFN-αs is their ability to inhibit cell growth, which is of major importance in determining anti-tumor action. Growth inhibition assays are well established, and usually depend on cell counts or uptake of tritiated thymidine ([$^3$H]thymidine) or another radiolabel. The human lymphoblastoid Daudi cell line has proven to be extremely sensitive to IFN-αs, and it has been used to measure antiproliferative activity in many IFN-αs and derived hybrid polypeptides (Meister et al., 1986). Use of this cell line has been facilitated by its ability to be grown in suspension cultures (Evinger and Pestka, 1981).

IFN-αs also exhibit many immunomodulatory activities (Zoon et al., 1986).

Although IFNs were first discovered by virologists, their first clinical use (in 1979) was as therapeutic agents for myeloma (Joshua et al., 1997). IFN-αs have since been shown to be efficacious against a myriad of diseases of viral, malignant, angiogenic, allergic, inflammatory, and fibrotic origin (Tilg, 1997). For instance, IFN-α is the only drug that is currently approved for treatment of hepatitis C in Europe and North America (Moussalli et al., 1998), and is the treatment of choice for chronic acute hepatitis B and AIDS-related Karposi's sarcoma. It has also proven efficacious in the treatment of metastatic renal carcinoma and chronic myeloid leukemia (Williams and Linch, 1997). Clinical uses of IFNs are reviewed in Gresser (1997) and Pfeffer (1997).

Standard recombinant techniques have become useful methods for the production and modification of IFN-α proteins (Streuli et al., 1981; Horisberger and Di Marco 1995; Rehberg et al., 1982; Meister et al., 1986; Fidler et al., 1987; Sperber et al., 1993; Mitsui et al., 1993; Muller et al., 1994; and Zav'Yalov and Zav'Yalov 1997). One such recombinant modification is the formation of hybrid IFN molecules. Hybrid IFNs contain fragments of two or more different interferon polypeptides, functionally fused together. The first IFN-α hybrids were designed to study molecular structure-function relationships. Much research has since been directed toward the production of hybrid IFNs that combine different biological properties of the parental proteins. Some hybrid IFNs display biological activity that is significantly different from that of both parent molecules (Horisberger and Di Marco 1995). For instance, certain early IFN-α/IFN-α hybrids acquired the novel property of very high activity on mouse cells (Streuli et al., 1980; Rehberg et al., 1982).

The techniques used by researchers to generate hybrid IFN polypeptides have evolved through time (Horisberger and Di Marco 1995). Early researchers took advantage of the presence of naturally occurring restriction endonuclease (RE) cleavage sites within IFN-encoding sequences to piece together homologous coding fragments. (See, for instance, U.S. Pat. No. 5,071,761 "Hybrid Interferons"). Though convenient, this was a limited method in that only so many of such pre-existing RE sites occurred in each IFN coding sequence. In addition, the location of each restriction site was fixed, making the possible combinations relatively small. More recently, researchers have used PCR amplification to create specific desired nucleic acid fragments, thereby gaining the ability to piece together new pieces of different IFNs (Horton et al., 1989).

A number of U.S. patents discuss various hybrid IFNs, how to produce them, and how to use them to treat patients. Many such patents relate to inter-group (multi-class) hybrid IFNs, wherein portions of the final hybrid are taken from at least two different interferon classification groups (e.g., α and β). For instance, U.S. Pat. No. 4,758,428 ("Multiclass hybrid interferons") describes the multi-class hybrid IFN HuIFN-α1 (1-73)/HuIFN-β1(74-166), and its use in pharmaceutical compositions to treat viral infections and tumorous growths in animal patients. Another such patent (U.S. Pat. No. 4,914,033 "Structure and properties of modified interferons") discloses the making of constructs that encode hybrid interferons comprising amino- and carboxy-terminal fragments of HuIFN-β fused to an internal sequence (amino acid residues 36-46) of a HuIFN-α. This patent also discloses the purification of the encoded hybrid IFN polypeptide and its use in pharmaceutical formulations.

Intra-group hybrid interferons (e.g., α1/α8 hybrids) have also been described. U.S. Pat. No. 5,071,761 ("Hybrid interferons") provides a good example of such intra-group hybrids. This patent discloses the construction, purification, use, and pharmaceutical preparation of various fusions hybrids between HuIFN-α1 and HuIFN-α8, where as many as four distinct IFN-α fragments have been used to construct the fusion. The construction, purification, and use of similar IFN-α hybrids to treat animal patients are disclosed in U.S. Pat. No. 5,137,720 ("Antiviral combination, and method of treatment").

It is to such engineered, recombinant intra-group hybrid interferon molecules that the present invention is directed.

SUMMARY OF THE INVENTION

The present invention provides hybrid interferons constructed by combining portions of two or more interferon-α xs, and mutant and mutant hybrid interferons constructed by point mutagenesis. These interferon molecules have good antiviral and antiproliferative activities. Thus, they may be used clinically to treat viral infections (such as influenza, rabies, and hepatitis B) and tumors, including but not limited to osteogenic sarcoma, multiple myeloma, nodular, poorly differentiated lymphoma, leukemia, carcinoma, melanoma, and papilloma, as well to modulate the immune system.

Six of the hybrids provided by this invention are termed HY-1, HY-2, HY-3, HY-4, HY-5, and HY-6, and are composed as follows:

HY-1: IFN-α21b(1-75)/IFN-α2c(76-166);
HY-2: IFN-α21b(1-95)/IFN-α2c(96-166);
HY-3: IFN-α2c(1-95)/IFN-α21b(96-166);
HY-4: IFN-α-21b(1-75)/IFN-α2c(76-81)/IFN-α21b(82-95)/IFN-α2c(96-166);
HY-5: IFN-α21b(1-75)/IFN-α21b(76-81)/IFN-α2c(82-95)/IFN-α2c(96-166);
HY-6: IFN-α21b(1-75)/IFN-α2c(76-95)/IFN-α21b(96-166).

This nomenclature indicates that HY-1 is comprised of amino acids 1-75 of IFN-α21b fused to amino acids 76-166 of IFN-α2c; HY-2 is comprised of amino acids 1-95 of IFN-α21b fused to amino acids 96-166 of IFN-α2c; HY-3 is comprised of amino acids 1-95 of IFN-α2c fused to amino acids 96-166 of IFN-α21b; and so forth for the remaining mutants. HY-3 is 165 amino acids long due to facilitated alignment numbering, as explained below.

Further aspects of the invention include the hybrid IFNs HY-1, HY-2, HY-3, HY-4, HY-5, and HY-6 and nucleic acid molecules that encode these hybrid interferons. Also encompassed within the scope of the invention are recombinant vectors that comprise such a nucleic acid molecule. Such vectors can be transformed into various cells to gain expression of these hybrid interferons. Accordingly, the invention also encompasses a cell transformed with a recombinant vector comprising such a nucleic acid molecule.

While each of these hybrids has particular advantages for clinical use, HY-3 in particular shows striking antiproliferative activity. This activity is associated with the combination of the 76-95 region of IFN-α2c and the 96-166 region of IFN-α21b. Accordingly, another aspect of the invention comprises HY-3-like molecules comprising such IFN components. Such molecules may be represented as X-A-B wherein "X" comprises about amino acid residues 1-75 of any IFN-α, "A" comprises about amino acid residues 76-95 of IFN-α2c and "B" comprises about amino acid residues 96-166 of IFN-α21b. While precise numerical limitations for the size of these sub-regions are provided (e.g., about amino acid residues 76-95), one of ordinary skill in the art will appreciate that these biological molecules may be varied in exact size. In certain embodiments, such variations will be no greater than plus or minus five amino acids from the specified termination points. Likewise, residues 81-90 or 81-95 of IFN-α2c comprise about the same amino acid residues as residues 76-95.

Strong antiproliferative activity may also be obtained by combining about IFN-α2c(76-95) with amino- and carboxy-regions of other IFNs. In such hybrids, the amino- (about residues 1-75) and carboxy- (about residues 96-166) regions may be provided from a single IFN-α, or from two different IFN-αs. These hybrid IFN molecules may be represented as X-A-Y, wherein "X" comprises about amino acid residues 1-75 of any IFN-α, "A" comprises about amino acid residues 76-95 of IFN-α2c, and "Y" comprises about amino acid residues 96-166 of any IFN-α. Another aspect of the invention is a recombinant IFN hybrid protein comprising first, second, and third domains, wherein the first domain comprises the amino-region of an IFN-α, the second domain comprises the middle region of IFNα2c (about residues 76-95), and the third domain comprises the carboxy-region of an IFN-α.

In certain embodiments of the invention, a shorter region of IFN-α2c contained within the region from residue 76 to residue 95 will be sufficient to confer substantial antiproliferative activity on a hybrid interferon containing such a fragment. The amino- and carboxy-terminal regions are provided from a single IFN-α or from two different IFN'αs. Such a hybrid interferon-α molecule with a short IFN-α2c middle region may be represented as V-C-Y, wherein "V" comprises about amino acid residues 1-81 of an interferon-α, "C" comprises about amino acid residues 82-95 of IFN-α2c, and "Y" comprises about amino acid residues 96-166 of an interferon-α.

In particular embodiments of the invention, the third domain of the protein comprises about amino acid residues 96-166 of IFN-α21b. In these embodiments, the first domain of the protein comprises the amino-region of any IFN-α. Such a hybrid IFN can be represented generally as X-A-B, wherein "X" comprises about amino acid residues 1-75 of an interferon-α, "A" comprises about amino acid residues 76-95 of IFN-α2c, and "B" comprises about amino acid residues 96-166 of IFN-α21b.

Hybrid interferon molecules according to the present invention can also contain more than three segments or domains of different parental interferons. Such multiple domains are taken from at least two different source or parental interferons, and may be taken from up to as many different interferon-αs as there are segments assembled to construct the hybrid. For instance, a four-domain hybrid interferon-α will be constructed from as few as two or as many as four different interferon-αs.

One four domain hybrid interferon-α molecule encompassed within the current invention can be designated M-N-O-P, wherein "M" comprises about amino acid residues 1-75 of interferon α21b, "N" comprises about amino acid residues 76 to 81 of interferon-α 2c, "O" comprises about amino acid residues 82 to 95 of interferon-α 21b, and "P" comprises about amino acid residues 96 to 166 of interferon-α 2c. A representative four domain hybrid interferon-α of this type is HY-4.

If a parental interferon that has one or more point or short deletions (as found with the 44$^{th}$ position in IFN-α2c) is used in construction of any of the hybrid interferons disclosed herein (e.g., those represented generally as X-A-B, X-A-Y, V-C-Y, or M-N-O-P), the numbering of the resultant hybrid fusions should be carried out using the facilitated alignment system.

The invention also provides nucleic acid molecules that encode any of the multi-domain hybrid IFN proteins disclosed herein, including those that can be represented generally as X-A-B, X-A-Y, V-C-Y, and M-N-O-P, as well as recombinant vectors that comprise such a nucleic acid molecule and cells transformed with such a vector.

One of ordinary skill in the art will also appreciate that minor modifications to the IFN-αsequences described herein may also be employed, such as amino acid substitutions, additions, and deletions, to create a mutant hybrid interferon-α. Thus, it is entirely possible that hybrid IFNs having greater than or fewer than 166 amino acids may be produced. Substitutions will typically be conservative in nature (e.g., one aliphatic amino acid for another), and such modifications will generally be designed not to have a significant effect on the biological properties of the hybrid IFN.

Also encompassed are purified or isolated interferon-αs (such as IFN-α2c) that contain point mutations at either residue 86 or residue 90, thereby changing these residues to tyrosine. Such mutant interferon-αs may be mutant hybrid molecules, and such mutant hybrids can contain short or long segments of IFN-α2c, IFN-α21b, or both of these parental interferons. Specific representatives of these mutant hybrid interferons include SDM-1 and SDM-2. Additional mutations can be made to replace existing tyrosine residues at 86 or 90 with other amino acids; specific representatives of this type of mutant hybrid interferon are SDM-3, and SDM-4.

Further aspects of the invention include nucleic acid molecules that encode the mutant hybrid interferons as disclosed herein, and particularly SDM-1, SDM-2, SDM-3, and SDM-4. Recombinant vectors that comprise such a nucleic acid molecule are also encompassed. Such vectors can be transformed into various cells to gain expression of these mutant interferons. Accordingly, the invention also encompasses a cell transformed with a recombinant vector comprising such a nucleic acid molecule.

The invention further provides pharmaceutical compositions comprising a pharmaceutically acceptable vehicle or carrier and at least one hybrid IFN-α polypeptide as described above. Such hybrid IFN-αs include those generally represented as X-A-Y, as X-A-B, as V-C-Y, and as M-N-O-P, as well as the specific hybrids HY-1, HY-2, HY-3, HY-4, HY-5, and HY-6. Mutant hybrid IFN-αs (e.g., SDM-1, SDM-2, SDM-3, or SDM-4) may also be included in such pharmaceutical compositions, either singly, in combinations with other mutant hybrid interferons, or in combination with hybrids IFNs as listed above.

These pharmaceutical compositions can be administered to humans or other animals on whose cells they are effective, in various manners such as topically, orally, intravenously, intramuscularly, intraperitoneally, intranasally, intradermally, intrathecally, and subcutaneously. Accordingly, a further aspect of the invention is such a pharmaceutical composition that is an injectable composition.

The invention also encompasses methods for treating a patient for a viral disease, comprising administering to the patient a therapeutically effective, viral disease-inhibiting amount of one or more hybrid or mutant hybrid interferon-αs as described above. One specific aspect of this invention is a method of treatment, wherein the hybrid interferon-α is administered to the patient by injection.

Another aspect of the invention encompasses methods for regulating cell growth in a patient, comprising administering to the patient a therapeutically effective, cell growth-regulating amount of one or more hybrid or mutant hybrid interferon-αs as described above. The cell growth regulated by this treatment may be, for instance, tumor cell growth. One specific aspect of this invention is a method of regulating cell growth, wherein the hybrid or mutant hybrid interferon-α is administered to the patient by injection.

BRIEF DESCRIPTION OF THE DRAWINGS

FIG. 1 shows the general PCR strategy used to construct interferon-α hybrids.

Figure 4A:
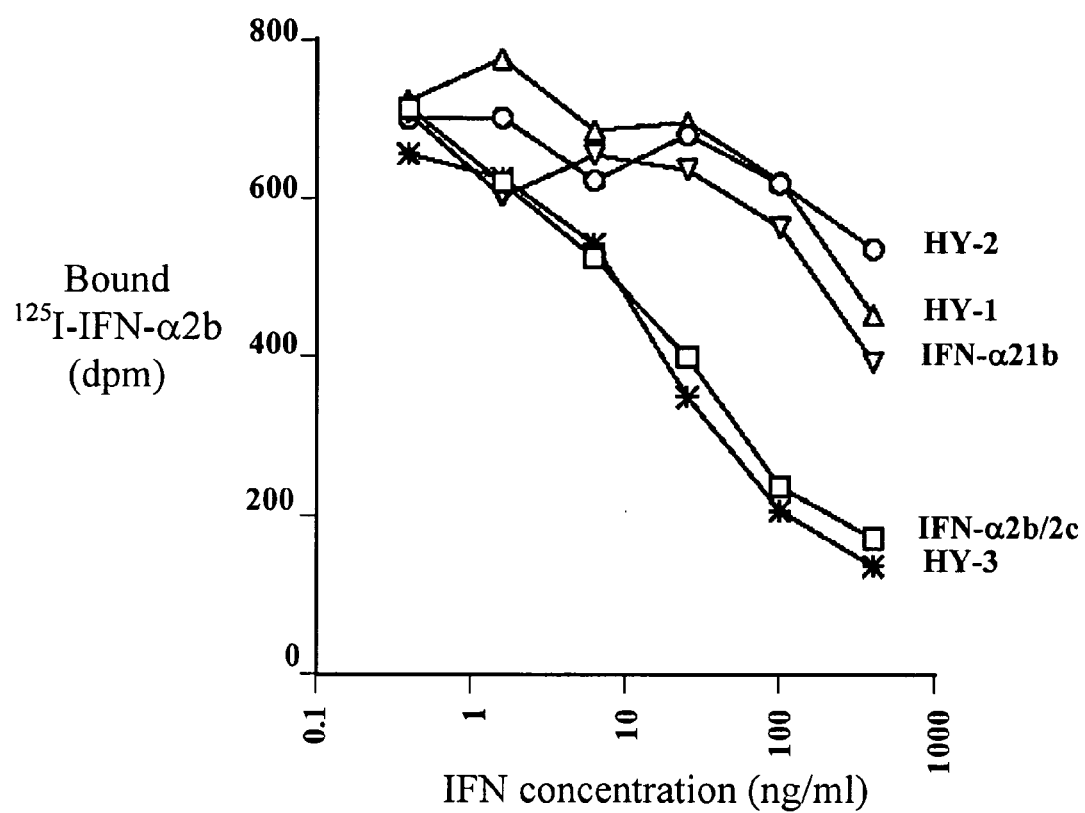
Figure 4B:
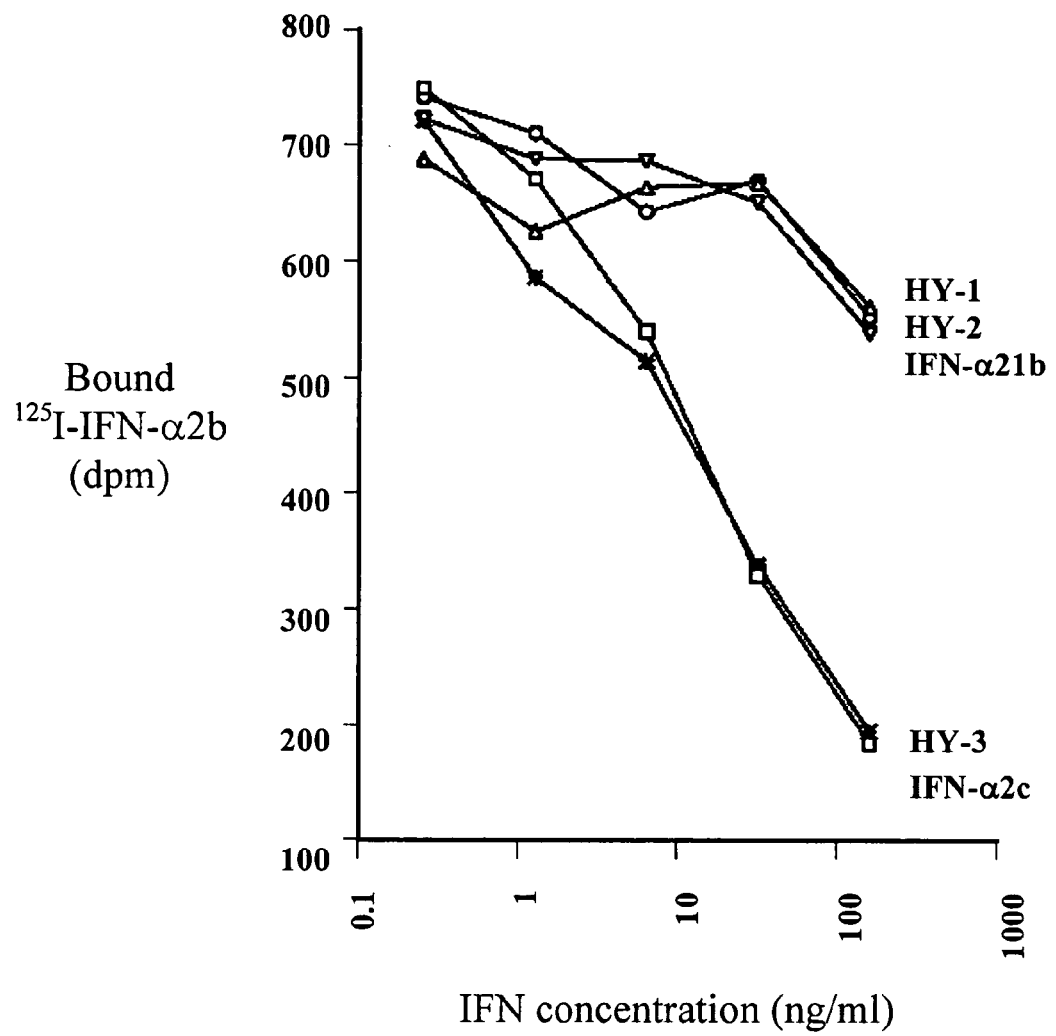

FIG. 4 shows the competitive binding curves for $^{125}$I-labeled IFN-α2b using native interferons IFN-α2c (□) and IFN-α21b (▽), and hybrid interferons HY-1 (△), HY-2 (O) and HY-3 (*) as competitors. Panel A, Daudi cells; Panel B, WISH cells.

FIG. 5 shows the amino acid sequences of IFN-α2c (accession number P01563), IFN-α21 (accession number X00145) and IFN-α hybrids, HY-1 (SEQ ID NO: 9; accession number AF085803), HY-2 (SEQ ID NO: 11; accession number AF085804) and HY-3 (SEQ ID NO: 13; accession number AF085805). Shaded residues differ between IFN-α2c and IFN-α21b. The asterisk (*) at apparent position 44 in the sequences of IFN-α2c and HY-3 has been inserted to facilitate alignment of the hybrid sequences and make subsequent position numbering consistent.

Table 1 summarizes the results of antiproliferative, antiviral, and competitive binding activity assays using parental IFNs α2 and α21b, hybrids HY-1, HY-2, HY-3, HY-4, and HY-5, and interferon mutant hybrids SDM-1, SDM-2, SDM-3, and SDM-4. Antiproliferative activities are reported as the amount (ng/ml) of each IFN species needed to inhibit cell growth by 50%. N/D: No Data.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but it is understood that the complementary strand is included by any reference to the displayed strand.

SEQ ID NO: 1 shows the outside PCR primer used for synthesis of hybrids HY-1, HY-2, HY-3, HY-4, HY-5, and HY-6, and mutant hybrids SDM-1, SDM-2, SDM-3, and SDM-4. This primer contains an engineered BamHI restriction site, and was used as the upstream primer during IFN-α21b (HY-1 and HY-2) and IFN-α2c (HY-3) amplification. This primer was also used as the upstream primer for amplification of IFN-α21b from cDNA.

SEQ ID NO: 2 shows the inside PCR primer used for synthesis of HY-1. This primer was used as the downstream primer during IFN-α21b amplification.

SEQ ID NO: 3 shows the inside PCR primer used for synthesis of HY-1. This primer was used as the upstream primer during IFN-α2c amplification.

SEQ ID NO: 4 shows the outside PCR primer used for synthesis of HY-1 and HY-2. This primer contains an engineered SpHI restriction site, and was used as the downstream primer during IFN-α2c amplification.

SEQ ID NO: 5 shows the inside PCR primer used for synthesis of HY-2 and HY-3. This primer was used as the downstream primer during IFN-α21b amplification.

SEQ ID NO: 6 shows the inside PCR primer used for synthesis of HY-2 and HY-3. This primer was used as the downstream primer during IFN-α21b amplification.

SEQ ID NO: 7 shows the outside PCR primer used for synthesis of HY-3. This primer contains the engineered SpHI restriction site, and was used as the downstream primer during IFN-α2c (HY-2) and IFN-α21b (HY-3) amplification. This primer was also used as the downstream primer for amplification of IFN-α21b from cDNA.

SEQ ID NO: 8 shows the DNA coding sequence and corresponding amino acid sequence of HY-1.

SEQ ID NO: 9 shows the amino acid sequence of HY-1.

SEQ ID NO: 10 shows the DNA coding sequence and corresponding amino acid sequence of HY-2.

SEQ ID NO: 11 shows the amino acid sequence of HY-2.

SEQ ID NO: 12 shows the DNA coding sequence and corresponding amino acid sequence of HY-3.

SEQ ID NO: 13 shows the amino acid sequence of HY-3.

SEQ ID NOs: 14 and 15 show the inside primers used for synthesis of HY-4.

SEQ ID NOs: 16 and 17 show the inside primers used for synthesis of HY-5 SEQ ID NOs: 18 and 19 show the inside primers used for synthesis of HY-6.

SEQ ID NOs: 20 and 21 show the inside primers used for synthesis of SDM-1.

SEQ ID NOs: 22 and 23 show the inside primers used for synthesis of SDM-2.

SEQ ID NOs: 24 and 25 show the inside primers used for synthesis of SDM-3.

SEQ ID NOs: 26 and 27 show the inside primers used for synthesis of SDM-4.

SEQ ID NO: 28 Shows the outside primer used with SEQ ID NO: 1 for synthesis of HY-4, HY-5, HY-6, SDM-1, SDM-2, SDM-3, and SDM-4.

SEQ ID NO: 29 shows the DNA coding sequence and corresponding amino acid sequence of HY-4.

SEQ ID NO: 30 shows the amino acid sequence of HY-4.

SEQ ID NO: 31 shows the DNA coding sequence and corresponding amino acid sequence of HY-5.

SEQ ID NO: 32 shows the amino acid sequence of HY-5.

SEQ ID NO: 33 shows the DNA coding sequence and corresponding amino acid sequence of HY-6.

SEQ ID NO: 34 shows the amino acid sequence of HY-6.

SEQ ID NO: 35 shows the DNA coding sequence and corresponding amino acid sequence of SDM-1.

SEQ ID NO: 36 shows the amino acid sequence of SDM-1.

SEQ ID NO: 37 shows the DNA coding sequence and corresponding amino acid sequence of SDM-2.

SEQ ID NO: 38 shows the amino acid sequence of SDM-2.

SEQ ID NO: 39 shows the DNA coding sequence and corresponding amino acid sequence of SDM-3.

SEQ ID NO: 40 shows the amino acid sequence of SDM-3.

SEQ ID NO: 41 shows the DNA coding sequence and corresponding amino acid sequence of SDM-4.

SEQ ID NO: 42 shows the amino acid sequence of SDM-4.

The amino acid sequences of the hybrid IFNs are depicted without leader sequences. Such leader sequences are typically present on IFNs produced in eukaryotic cells, but are generally cleaved off to produce the mature form of the protein. The nomenclature for IFNs used herein is based on the amino acid sequences of mature IFNs.

DETAILED DESCRIPTION OF THE INVENTION

I. Definitions and Abbreviations
  A. Abbreviations

IFN: interferon

IFN-α: interferon-α

HuIFN-α: human interferon-α

IU: international units

MDBK: Madin-Darby bovine kidney cells

ATCC: American Type Culture Collection

*E. coli:* Escherichia coli

PHA: phytohemagglutinin

SDS-PAGE: sodium dodecyl sulfate-polyacrylamide gel electrophoresis poly-DI-DC: polydeoxyinosine-deoxycytosine RNase: ribonuclease RE: restriction endonuclease moi: multiplicity of infection B. Definitions Unless otherwise noted, technical terms are used according to conventional usage. Definitions of common terms in molecular biology may be found in Lewin, Genes V published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). The nomenclature for DNA bases and the three-letter code for amino acid residues, as set forth at 37 CFR § 1.822, are used herein. All interferon units are expressed with reference to the NIH human lymphoblastoid IFN standard Ga 23-901-532.

In order to facilitate review of the various embodiments of the invention, the following definitions of terms are provided. These definitions are not intended to limit such terms to a scope narrower than would be known to a person of ordinary skill in the field.

Interferons: A family of secreted polypeptides produced by a variety of eukaryotic cells upon exposure to various environmental stimuli, including virus infection or exposure to a mitogen. In addition to having antiviral properties, interferons have been shown to affect a wide variety of cellular functions. Interferons (IFNs) have been classified into four major groups according to their chemical, immunological, and biological characteristics: α, β, γ, and ω. Each IFN is further identified by the eukaryote in which it originated, with HuIFN indicating human interferon. For the purposes of this disclosure, any interferon that lacks a specific eukaryote source designation is presumed to be that set of equivalent interferons from any source. In other words, IFN-α2c would refer to the interferon-α 2c from any eukaryotic source, while HuIFN-α2c refers specifically to human interferon-α 2c. Throughout this specification, the IFN nomenclature provided by Allen and Diaz (1996) is employed unless otherwise noted.

Interferon-α (IFN-α) polypeptides are produced in, for instance, human leukocyte cells after exposure to viruses or double-stranded RNA, or in transformed leukocyte cell lines (e.g., lymphoblastoid lines). Most IFN-αs are non-glycosylated polypeptides of 165 or 166 amino acids, encoded for by a multigene family of at least 20 genes. The difference in length is due to an amino acid deletion at the $44^{th}$ position in certain IFNs, for instance IFN-α2c. Each gene (termed IFNA1, IFNA2, etc.) encodes a single IFN-α polypeptide subtype (termed IFN-α1, IFN-α2, etc., respectively). Amino acid sequence identity among IFN-αsubtypes is generally 80-85% (Horisberger and Di Marco 1995). Within each subtype, individual sequence variants (IFN species) are further denoted with an additional letter designation, e.g., IFN-α2a, IFN-α2b, and IFN-α2c. The sequence differences between these species are often very small (1-3 amino acids).

Hybrid interferons: Recombinant interferon molecules that combine various segments from parental interferon molecules. Hybrids may be constructed using portions of two (or more) IFNs from different IFN groups (e.g., one segment from an IFN-α polypeptide and another segment from an IFN-β polypeptide) (see, for instance, U.S. Pat. Nos. 4,758,428 "Multiclass hybrid interferons"; 4,914,033 "Structure and properties of modified interferons"; and 4,917,887 "Hybrid interferons, their use as pharmaceutical compositions and as intermediate products for the preparation of antibodies and the use thereof and processes for preparing them"). These are referred to as inter-group or multi-class hybrids. Alternatively, hybrids can be formed using portions of two different IFN species from one IFN group (e.g., one segment from each of two IFN-α polypeptides) (see, for instance, U.S. Pat. Nos. 4,806,347 "Interferon combinations"; 4,892,743 "Novel hybrid interferon species"; 5,071,761 "Hybrid interferons"; 5,137,720 "Antiviral combination, and method of treatment"; and 5,609,868 "Pharmaceutical compositions comprising hybrid α-interferon"). These are referred to as intra-group hybrids. The construction and properties of certain IFN-α/IFN-α hybrids has been reviewed (Horisberger and Di Marco 1995).

Herein, hybrid interferon protein nomenclature is used largely as proposed in Allen and Diaz (1996). For instance, the hybrid interferon fusion HY-1 is fully designated as IFN-α21b(1-75)/IFN-α2c(76-166), wherein the amino-terminal end of the polypeptide consists of amino acids 1-75 of IFN-α21b and the carboxy-terminal end consists of amino acids 76-166 of IFN-α2c. Hybrids HY-2 [IFN-α21b(1-95)/IFN-α2c(96-166)], HY-4 [IFN-α-21b(1-75)/IFN-α2c(76-81)/IFN-α21b(82-95)/IFN-α2c(96-166)], and HY-6 [IFN-α21b(1-75)/IFN-α2c(76-95)/IFN-α21b(96-166)] are designated similarly. The same terminology can be used where otherwise contiguous regions of the same parental interferon molecule are re-joined in a final construct, as is true in HY-5 [IFN-α21b(1-75)/IFN-α21b(76-81)/IFN-α2c(82-95)/IFN-α2c(96-166)].

One modification has been made to the nomenclature method of Allen and Diaz (1996), to facilitate consistent and simple numbering of hybrids constructed from interferons of different lengths where the length difference is due to relatively short internal insertions or deletions. For instance, IFN-α2c is one amino acid shorter than IFN-α21b due to the absence of an aspartate at the $44^{th}$ position in the sequence. The hybrid fusion interferon HY-3 [IFN-α2c(1-95)/IFN-α21b(96-166)], illustrates the "facilitated alignment" modification to the standard numbering system. HY-3 is in fact only 165 amino acids long, due to the "empty" place-saving designation at position 44.

This "facilitated alignment" numbering system is illustrated in FIG. 5. The asterisk (*) at apparent position 44 in the sequences of IFN-α2c and HY-3 has been inserted to facilitate alignment of the hybrid sequences and make subsequent residue position numbering consistent. In other words, this asterisk serves as a "place-saver" in the numbering of these sequences. This numbering system also could be used for sequences that differ by more than one residue in length, simply by inserting the appropriate number of "spacers" to force alignment of the remaining sequence.

If a parental interferon that has one or more point or short deletions (as found with the $44^{th}$ position in IFN-α2c) is used in construction of a hybrid, the numbering of the resultant hybrid fusions should be carried out using the facilitated alignment system.

It is possible to refer to general classes of hybrid IFN molecules by designating domains within the protein that are of interest. For instance, data indicate that it is likely the carboxy-terminal portion (residues 76-166) of HY-3 that is important for the observed high antiproliferative activity. A class of HY-3-like molecules that contains this carboxy-terminal portion can be represented generally as X-A-B, wherein "X" comprises about amino acid residues 1-75 of an interferon-α, "A" comprises about amino acid residues 76-95 of IFN-α2c, and "B" comprises about amino acid residues 96-166 of IFN-α21b.

One of ordinary skill in the art will appreciate that these elements may be combined to produce HY-3-like molecules without necessarily splicing the components in the same place. It is possible to use shorter or longer fragments of IFN-α2c, fused to correspondingly longer or shorter fragments of IFN-α21b. In such instances, the middle element of IFN-α2c used to construct the hybrid molecule comprises residues 76-96, 76-97 or 76-98, while the carboxy-terminal element of IFN-α21b would correspondingly comprise residues 97-166, 98-166, or 99-166, respectively. Any component that is spliced within 5 amino acid residues of the residue specified comprises about the same region. For instance, amino acid residues 1-80 or 1-70 of IFN-α2c comprise about the same amino acid residues as the component with residues 1-75. Likewise, residues 81-90 or 81-95 of IFN-α2c comprise about the same amino acid residues as this component with residues 76-95.

Further, hybrid interferon molecules can be constructed in which the middle region is defined as being from a specific source, for instance residues 76-95 of IFN-α2c, but the amino- and carboxy-regions can be chosen from any IFN-α. In such hybrids, the amino- (about residues 1-75) and carboxy- (about residues 96-166) regions may be provided from any single IFN-α, or from two different IFN-αs. These hybrid IFN molecules may be represented as X-A-Y, wherein "X" comprises about amino acid residues 1-75 of any IFN-α, "A" comprises about amino acid residues 76-95 of IFN-α2c, and "Y" comprises about amino acid residues 96-166 of any IFN-α. As above, any component that is spliced within 5 amino acid residues of the residue specified comprises about the same region. For instance, residues 81-90 or 81-95 of IFN-α2c, serving as the "A" component of this construct, comprise about the same amino acid residues as "A" with residues 76-95 of IFN-α2c.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers useful in this invention are conventional. Remington's Pharmaceutical Sciences, by E. W. Martin, Mack Publishing Co., Easton, Pa., 15th Edition (1975), describes compositions and formulations suitable for pharmaceutical delivery of the hybrid interferons herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Injectable composition: A pharmaceutically acceptable fluid composition comprising at least an active ingredient. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the hybrid interferons of this invention are conventional; appropriate formulations are well known in the art, and examples may be found in U.S. Pat. No. 5,609,868 ("Pharmaceutical compositions comprising hybrid α-interferon").

Therapeutically effective amount of IFN-α: A quantity of interferon-α sufficient to achieve a desired effect in a subject being treated. For instance, this can be the amount necessary to inhibit viral proliferation or to regulate cell, and more specifically tumor cell, proliferation. See, U.S. Pat. Nos. 4,089,400 ("Polypeptides and process for the production thereof") and 5,503,828 ("Alpha interferon composition and method for its production from human peripheral blood leukocytes") for general disclosure as to the amounts of IFN-α that have proven efficacious in clinical settings. The same dose levels as are used in conventional (non-hybrid) interferon therapy may be used with hybrid interferons. In general, a dose of about $10^5$ to $10^8$ IU will be appropriate and may be administered more than once, for example daily, during a course of treatment. However, the effective amount of hybrid IFN-α will be dependent on the subject being treated, the severity of the affliction, and the manner of administration of the interferon.

The hybrid interferons disclosed in the present invention have equal application in medical and veterinary settings. Therefore, the general term "subject being treated" is understood to include all animals that produce interferon polypeptides, including humans or other simians, dogs, cats, horses, and cows.

Probes and primers: A nucleic acid probe comprises an isolated nucleic acid attached to a detectable label or reporter molecule. Typical labels include radioactive isotopes, ligands, chemiluminescent agents, and enzymes. Methods for labeling and guidance in the choice of labels appropriate for various purposes are discussed, e.g., in Sambrook et al., (1989) and Ausubel et al., (1987).

Primers are short nucleic acids, preferably DNA oligonucleotides 15 nucleotides or more in length. Primers may be annealed to a complementary target DNA strand by nucleic acid hybridization to form a hybrid between the primer and the target DNA strand. The primer may be then extended along the target DNA strand through the use of a DNA polymerase enzyme. Primer pairs (one on either side of the target nucleic acid sequence) can be used for amplification of a nucleic acid sequence, e.g., by the polymerase chain reaction (PCR) or other nucleic-acid amplification methods known in the art.

Methods for preparing and using probes and primers are described, for example, in Sambrook et al., (1989), Ausubel et al., (1987), and Innis et al., (1990). PCR primer pairs can be derived from a known sequence, for example, by using computer programs intended for that purpose such as Primer (Version 0.5, © 1991, Whitehead Institute for Biomedical Research, Cambridge, Mass.). One of skill in the art will appreciate that the specificity of a particular probe or primer increases with its length. Thus, for example, a primer comprising 20 consecutive nucleotides of one human IFN-αsubtype cDNA or gene will anneal to a target sequence (e.g., a different human IFN-αsubtype or an IFN-α from another species) with a higher specificity than a corresponding primer of only 15 nucleotides. Thus, in order to obtain greater specificity, probes and primers may be selected that comprise 20, 25, 30, 35, 40, 50 or more consecutive nucleotides of one IFN-α subtype cDNA or gene sequence.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, particle gun acceleration, and the like.

Isolated: An "isolated" biological component (such as a nucleic acid or protein) has been substantially separated or purified away from other biological components in the cell of the organism in which the component naturally occurs, i.e., other chromosomal and extra-chromosomal DNA and RNA, and proteins. Thus, nucleic acids and proteins that have been "isolated" include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified IFN-α preparation is one in which the interferon-alpha is more enriched than the protein is in its natural environment within a cell. Preferably, a preparation of IFN-α is purified such that the IFN-α represents at least 50% of the total protein content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Recombinant: A recombinant nucleic acid is one that has a sequence that is not naturally occurring, or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, or a combination of these techniques. Similarly, a recombinant protein is one that is encoded by a recombinant nucleic acid.

II. Construction of Hybrid and Mutant Hybrid Interferon-αs

A. General Approaches to Hybrid Interferon-α Construction

The production of a number of hybrid IFNs has been reviewed by Horisberger and Di Marco (1995); this article provides a good overview of the process of construction of such molecules. Specific examples of methods for construction of hybrid interferons can be found, for example, in U.S. Pat. Nos. 4,892,743 ("Novel hybrid interferon species"); 5,071,761 ("Hybrid Interferons"); 4,758,428 ("Multiclass hybrid interferons"); and 4,716,217 ("Hybrid lymphoblastoid-leukocyte human interferons").

Generally, two procedures are used to create hybrid IFN-αs. First, some researchers have taken advantage of the presence of naturally occurring RE cleavage sites within IFN-encoding sequences to piece together homologous coding fragments. (See, for instance, U.S. Pat. No. 5,071,761 "Hybrid Interferons"). The second general procedure for construction of hybrid IFN-αs uses PCR amplification to create specific desired nucleic acid fragments, thereby gaining the potential to piece together new pieces of different IFNs (Horton et al., 1989). It is this second technique that has been employed herein to generate novel and useful IFN-α hybrids.

B. Construction of Parental Interferon-Bearing Plasmids

A plasmid bearing the IFN-α2c coding sequence (pBluescript/A2) was constructed as previously described (Hayes and Zoon, 1993).

To construct a plasmid bearing the coding sequence of IFN-α21b, a pair of oligonucleotides, SEQ ID NO: 1 and SEQ ID NO: 7, with BamHI and PstI restriction sites, were synthesized based on the cDNA coding region for mature human IFN-α21b protein (Genentech, South San Francisco, Calif.). These were used as primers in a standard polymerase chain reaction (PCR) (Innis et al., 1990), and the entire coding region for mature human IFN-α21b protein amplified. The resulting products were cleaved with restriction endonucleases (REs) BamHI and PstI and cloned into the E. coli expression vector pQE30 (QIAGEN, Chatsworth, Calif.) cleaved with REs BamHI and PstI, to form pQE30/A21. The final construct was verified by DNA sequence analysis (Sanger et al., 1977).

C. Construction of HY-1

Figure 1A:
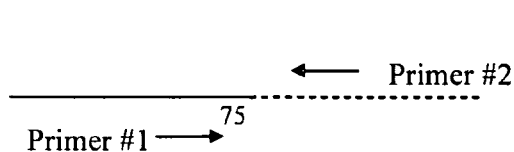
FIG. 1(A) shows the strategy for construction of HY-1.
Figure 1A:

The hybrid IFN cDNAs presented in this invention were constructed by PCR technology (Horton et al., 1989). The procedure used to construct HY-1 is illustrated in FIG. 1(A). In reaction one, primers 1 (SEQ ID NO: 1) and 2 (SEQ ID NO: 2) were used to amplify the amino-terminal portion of IFN-α21b (encoding amino acids 1-75), using linearized pQE30/A21 as template. In reaction two, primers 3 (SEQ ID NO: 3) and 4 (SEQ ID NO: 4) were used to amplify the carboxy-terminal portion of IFN-α2c (encoding amino acids 76-166), using linearized pBluescript/A2 as template. Purified DNA fragments from the first pair of PCR reactions were then mixed as templates for the second round of PCR, and the fused sequence amplified using primers 1 (SEQ ID NO: 1) and 4 (SEQ ID NO: 4). This reaction generated the full-length HY-1 fusion coding sequence (SEQ ID NO: 8), which encodes IFN-α21b(1-75)/IFN-α2c(76-166) (SEQ ID NO: 9).

Purified DNA fragments from the second round of PCR amplification were digested with REs BamHI and SpHI and ligated into pQE30. The final HY-1 construct (pHY-1) was verified by DNA sequence analysis (Sanger et al., 1977). HY-1 has been submitted to GenBank for publication on or after Jul. 7, 1999, accession number AF085803.

D. Construction of HY-2

Figure 1B:
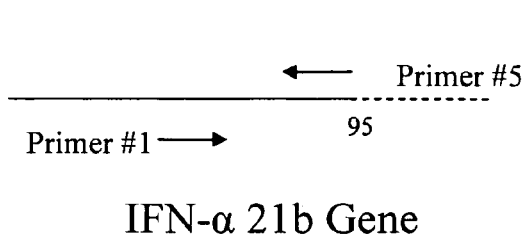
FIG. 1(B) shows the strategy for construction of HY-2.
Figure 1B:
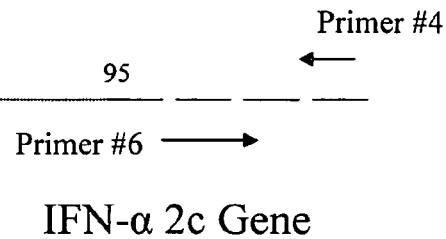
Figure 1B:
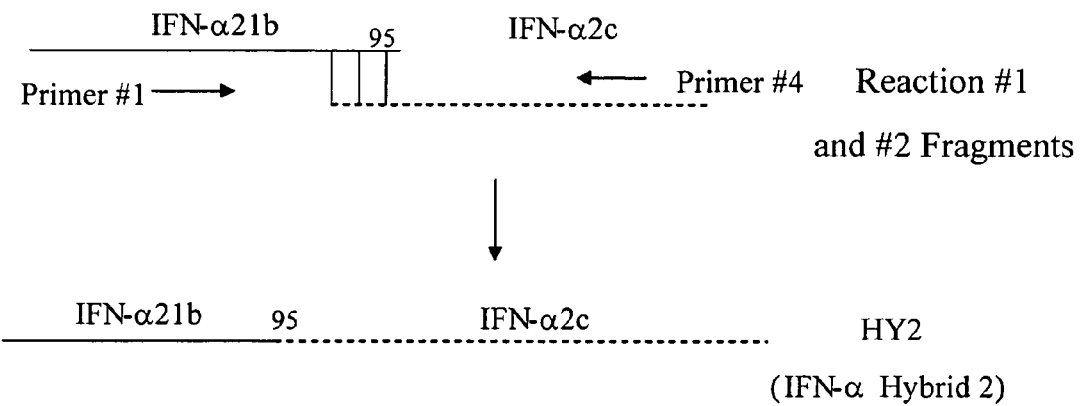

The procedure used to construct HY-2 is illustrated in FIG. 1(B). In reaction one, primers 1 (SEQ ID NO: 1) and 5 (SEQ ID NO: 5) were used to amplify the amino-terminal portion of IFN-α21b (encoding amino acids 1-95), using linearized pQE30/A21 as template. In reaction two, primers 6 (SEQ ID NO: 6) and 4 (SEQ ID NO: 4) were used to amplify the carboxy-terminal portion of IFN-α2c (encoding amino acids 96-166), using linearized pBluescript/A2 as template. Purified DNA fragments from the first pair of PCR reactions were then mixed as templates for the second round of PCR, and the fused sequence amplified using primers 1 (SEQ ID NO: 1) and 4 (SEQ ID NO: 4). This reaction generated the full-length HY-2 fusion coding sequence (SEQ ID NO: 10), which encodes IFN-α21 b(1-95)/IFN-α2c(96-166) (SEQ ID NO: 11).

Purified DNA fragments from the second round of PCR amplification were digested with BamHI and SpHI and ligated into pQE30. The final HY-2 construct (pHY-2) was verified by DNA sequence analysis (Sanger et al., 1977). HY-2 has been submitted to GenBank for publication on or after Jul. 7, 1999, accession number AF085804.

E. Construction of HY-3

Figure 1C:
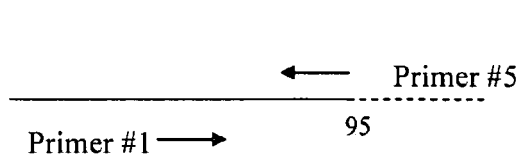
FIG. 1(C), that for HY-3 construction.
Figure 1C:
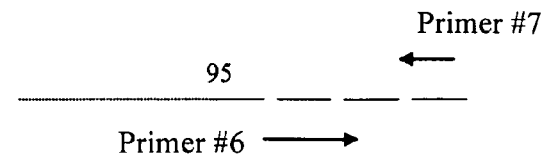
Figure 1C:
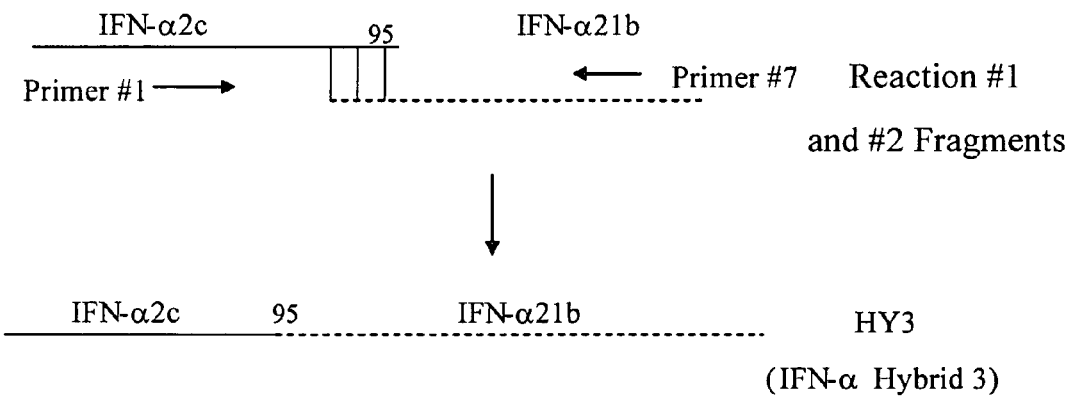

The procedure used to construct HY-3 is illustrated in FIG. 1(C). In reaction one, primers 1 (SEQ ID NO: 1) and 5 (SEQ ID NO: 5) were used to amplify the amino-terminal portion of IFN-α2c (encoding amino acids 1-95;because of the facilitated alignment method that assigns the "absent" position 44 a number, this fragment is only 94 amino acids long), using linearized pQE30/A21 as template. In reaction two, primers 6 (SEQ ID NO: 6) and 7 (SEQ ID NO: 7) were used to amplify the carboxy-terminal portion of IFN-α21b (encoding amino acids 96-166), using linearized pBluescript/A2 as template. Purified DNA fragments from the first pair of PCR reactions were then mixed as templates for the second round of PCR, and the fused sequence amplified using primers 1 (SEQ ID NO: 1) and 7 (SEQ ID NO: 7). This generated the full-length HY-3 fusion coding sequence (SEQ ID NO: 12), which encodes IFN-α2c(1-95)/IFN-α21b(96-166) (SEQ ID NO: 13) (which is in fact only 165 amino acids long).

Purified DNA fragments from the second round of PCR amplification was digested with BamHI and SpHI and ligated into pQE30. The final HY-3 construct (pHY-3) was verified by DNA sequence analysis (Sanger et al., 1977). HY-3 has been submitted to GenBank for publication on or after Jul. 7, 1999, accession number AF085805.

F. Construction of HY4, -5, and 6

Using methods essentially similar to those discussed above for HY-1, -2, and -3, three further hybrid interferon molecules were constructed which incorporate shorter internal segments of the parent interferons. HY-4 was constructed using HY-2 as a template, and incorporates the following α-interferon sequences: IFN-α21b(1-75)/IFN-α2c(76-81)/IFN-αc21b(82-95)/IFN-α2c(96-166). The nucleotide sequence of HY4 is depicted in SEQ ID NO: 29. Primers 14s and 14 as (SEQ ID NO: 14 and 15) served as the inside primers for construction of this hybrid.

HY-5 was constructed using HY-2 as a template, and incorporates the following interferon sequences: IFN-α21b (1-75)/IFN-α21b(76-81)/IFN-α2c(82-95)/IFN-α2c(96-166). The nucleotide sequence of HY-5 is depicted in SEQ ID NO: 31. Primers 15s and 15 as (SEQ ID NO: 16 and 17) served as the inside primers for construction of this hybrid.

HY-6 was constructed using HY-1 and parental IFN-α21b as templates, and incorporates the following interferon sequences: IFN-α21b(1-75)/IFN-α2c(76-95)/IFN-α21b(96-166). The nucleotide sequence of HY-6 is depicted in SEQ ID NO: 33. Primers M291s and M219 as (SEQ ID NO: 18 and 19) served as the inside primers for construction of this hybrid. Primers 28 and 1 (SEQ ID NO: 28 and 1) served as the outside primers for production of all three of these hybrids.

G. Construction of Mutant Hybrid Interferon-αs SDM-1, SDM-2, SDM-3, and SDM-4

In addition to the production of hybrid interferons from native sequences, it is also possible to construct hybrids that have specific sequence mutations at specific nucleotide and/or amino acid residues. As an example of this, four mutant interferon hybrids were constructed using methods essentially similar to those used above to construct the base hybrids. Mutations in specific amino acids were introduced into these mutant hybrids by incorporating desired nucleotide changes into the primers used for amplification of the relevant hybrid sequences.

SDM-1 was constructed using HY-4 as the template, and integrates a single amino acid mutation at residue 86, which changes the serine found in the IFN-α21b sequence to a tyrosine. The nucleotide sequence of SDM-1 is depicted in SEQ ID NO: 35. Primers SDM1s and SDM1 as (SEQ ID NO: 20 and 21) served as the inside primers for construction of this mutant.

SDM-2 was constructed using HY-4 as the template, and integrates a single amino acid mutation at residue 90, which changes the asparagine found in the IFN-α21b sequence to a tyrosine. The nucleotide sequence of SDM-2 is depicted in SEQ ID NO: 37. Primers SDM2s and SDM2 as (SEQ ID NO: 22 and 23) served as the inside primers for this mutant.

SDM-3 was constructed using HY-5 as the template, and integrates a single amino acid mutation at residue 86, which changes the tyrosine found in the IFN-α2c sequence to a serine. The nucleotide sequence of SDM-3 is depicted in SEQ ID NO: 39. Primers SDM3s and SDM3 as (SEQ ID NO: 24 and 25) served as the inside primers for this mutant.

SDM-4 was constructed using HY-5 as the template, and integrates a single amino acid mutation at residue 90, which changes the tyrosine found in the IFN-α2c sequence to an asparagine. The nucleotide sequence of SDM-4 is depicted in SEQ ID NO: 41. Primers SDM4s and SDM4 as (SEQ ID NO: 26 and 27) served as the inside primers for this mutant. Primers 2* and 1 (SEQ ID NO: 28 and 1) served as the outside primers for production of all four mutants.

III. Expression and Purification of Hybrid and Mutant Hybrid Interferons

A. Expression of IFN-α Hybrids and Mutants

The following method of expression of hybrid and mutant interferons is provided merely by way of example. One skilled in the art will understand that there are myriad ways to express a recombinant protein such that it can be subsequently purified. See, for instance, U.S. Pat. No. 5,089,400 ("Polypeptides and process for the production thereof"). In general, an expression vector carrying the nucleic acid sequence that encodes the desired protein will be transformed into a microorganism for expression. Such microorganisms can be prokaryotic (bacteria) or eukaryotic (e.g., yeast). One appropriate species of bacteria is *Escherichia coli* (*E. coli*), which has been used extensively as a laboratory experimental expression system. A eukaryotic expression system will be preferred where the protein of interest requires eukaryote-specific post-translational modifications such as glycosylation.

The expression vector can include a sequence encoding a targeting peptide, positioned in such a way as to be fused to the coding sequence of the IFN. This allows the hybrid IFN to be targeted to specific locations. In a prokaryotic expression system, a signal sequence can be used to secrete the newly synthesized hybrid protein. In a eukaryotic expression system, the targeting peptide would specify targeting of the hybrid protein to one or more specific sub-cellular compartments, or to be secreted from the cell, depending on which peptide is chosen. One such appropriate targeting peptide is the native IFN signal peptide, which would direct the hybrid IFN to be secreted from eukaryotic cells.

Vectors suitable for stable transformation of bacterial cells are well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site. For production of large amounts of recombinant proteins, an inducible promoter is preferred. This permits selective production of the recombinant protein, and allows both higher levels of production than constitutive promoters, and enables the production of recombinant proteins that may be toxic to the expressing cell if expressed constitutively.

In addition to these general guidelines, protein expression/purification kits have been produced commercially. See, for instance, the QIAexpress™ expression system from QIAGEN (Chatsworth, Calif.) and various expression systems provided by INVITROGEN (Carlsbad, Calif.). Depending on the details provided by the manufactures, such kits can be used for production and purification of the disclosed hybrid interferons.

The following procedure can be used to express hybrid interferons as disclosed herein. Plasmid DNA molecules carrying parental interferons IFNA-b 2 (pBluescript/A2) and IFNA21 (pQE30/A21), and hybrid interferons HY-2 (pHY-2) and HY-3 (pHY-3) are transformed into *E. coli* strain SG13009 [pREP4] (QIAGEN, Chatsworth, Calif.). pHY-1 plasmid DNA is transformed into *E. coli* strain DH5αF'IQ (Gibco BRL, Gaithersburg, Md.). Bacteria are grown overnight in LB broth containing 100 μg/ml ampicillin (pHY-1) or 100 μg/ml ampicillin and 25 μg/ml kanamycin (pHY-2, pHY-3, pBluescript/A2 and pQE30/A21) in a 37° C. shaker incubator. The cultures are diluted 1:50 in LB Broth containing the appropriate antibiotic(s) and incubated at 37° C. with shaking, to a cell density of 0.8-0.9 $A_{600}$. Protein expression is induced by the addition of 2 mM isopropyl-1-thio-β-D-galactopyranoside (IPTG). The bacteria are then incubated at 30° C. for 4-5 hours, after which cells were harvested and lysed by sonication. Each cell lysate is clarified by centrifugation at 10,000×g for 30 minutes at 4° C. The resultant supernatants are used for subsequent purification of IFN polypeptides.

B. Purification of Interferon Hybrids and Mutants

One skilled in the art will understand that there are myriad ways to purify recombinant interferon polypeptides. Typical methods of protein purification may be used to purify the disclosed interferons. Such methods include, for instance, monoclonal antibody affinity chromatography and isolation of insoluble protein inclusion bodies after over production. In addition, purification affinity-tags, for instance a hexa-histidine sequence, may be recombinantly fused to the protein and used to facilitate polypeptide purification. For further examples of purification of interferons, see U.S. Pat. No. 5,089,400 ("Polypeptides and process for the production thereof") and Zoon et al., (1992).

In additional to the general protein purification procedures, certain modifications specific to interferon purification of may be beneficial. See for instance U.S. Pat. No. 5,593,667 ("Recombinant immune interferon having an intact carboxyl terminus"), disclosing IFN extraction techniques that overcome certain difficulties associated with degradation of the carboxy-terminal region of interferons during extraction and purification.

Commercially produced protein expression/purification kits provide tailored protocols for the purification of proteins made using each system. See, for instance, the QIAexpress™ expression system from QIAGEN (Chatsworth, Calif.) and various expression systems provided by INVITROGEN (Carlsbad, Calif.). Where a commercial kit is employed to produce the hybrid interferons, the manufacturer's purification protocol is a preferred protocol for purification of that hybrid. For instance, proteins expressed with an amino-terminal hexa-histidine tag can be purified by binding to nickel-nitrilotriacetic acid (Ni—NTA) metal affinity chromatography matrix (*The QIAexpressionist*, QIAGEN, 1997)

By way of example only, the following procedure can be used to purify hybrid interferons. Expression of parental interferons IFN-α2c and IFN-α21b, and three IFN hybrids (HY-1, -2, and -3) is obtained in *E. coli* using the QIAexpress™ expression system plasmid pQE30. IFN polypeptide purification is first performed by Ni—NTA-Agarose resin metal-affinity chromatography (The QIAexpressionist, QIAGEN, 1997; Janknecht et al., 1991). The specific antiviral activity of this partially purified material ranges from $3 \times 10^6$ IU/mg protein to $4.5 \times 10^6$ IU/mg protein on Madin-Darby bovine kidney (MDBK) cells (ATCC #: CCL-22). To attain higher specific activity, the IFN-αs may optionally be further purified by monoclonal antibody affinity chromatography (e.g., 4F2, NK2) (Zoon et al., 1992). Final specific activities of each IFN species are shown in Table 1. Generally, activities range from $2 \times 10^8$ IU/mg protein to $3.7 \times 10^8$ IU/mg protein on MDBK cells and from $0.1 \times 10^8$ IU/mg protein to $1.9 \times 10^8$ IU/mg protein on WISH cells (ATCC #: CCL-25). Purified recombinant protein concentrations are determined using the Coomassie Plus protein assay (PIERCE, Rockford, Ill.). Purity of the recombinant IFN-αs can be assessed by SDS-PAGE and HPLC analysis.

Similar procedures can be used to produce and purify the interferon hybrids HY-4, -5, and -6, as well as mutant interferon hybrids SDM-1, -2, -3, and -4.

IV. Activity of Hybrid and Mutant Hybrid Interferons

A. Antiproliferative Activity

The antiproliferative activities of several purified IFN-α hybrids and mutant hybrids were compared to parental interferons IFN-α21b and IFN-α2c. The ability of the IFN-α hybrids, mutants and both parents to inhibit the growth of Daudi, WISH and primary human lymphocyte cells was compared.

Human Daudi cells that are sensitive to IFN were obtained from Dr. P. Grimley, Dept. of Pathology, USUHS, Bethesda Md. Cells were grown in suspension using RPMI 1640 with 10% fetal calf serum (FCS), 2 mM glutamine and 0.2% gentamicin. WISH cells as above were grown as monolayer cultures using Eagle's minimal essential medium supplemented with 10% FCS and gentamicin (50 μg/ml).

The cultures were incubated at 37° C. in a humidified atmosphere containing 5% $CO_2$. All cultures were free of mycoplasma.

Antiproliferative assays on Daudi cells were performed as previously described (Hu et al., 1993). The assays on WISH cells were performed by incubating the cells with various IFN-αs at concentrations ranging from 0.0003 ng/ml to 300 ng/ml for 72 hours at 37° C. A 50 μl aliquot of 2 mg/ml 3-[4,5-dimethylthiazol-2-yl]-2,5-diphenyl tetrazolium bromide (MTT) was added into each well and incubated for 4 hours at 37° C. Then, 10% SDS in 0.01 N HCl (250 μl) was added to each well and incubated overnight at 37° C. The $OD_{570}$ of each well was determined, and the percentage of growth inhibition was calculated by comparing control (untreated) cultures with the IFN-treated cultures.

Figure 2A:
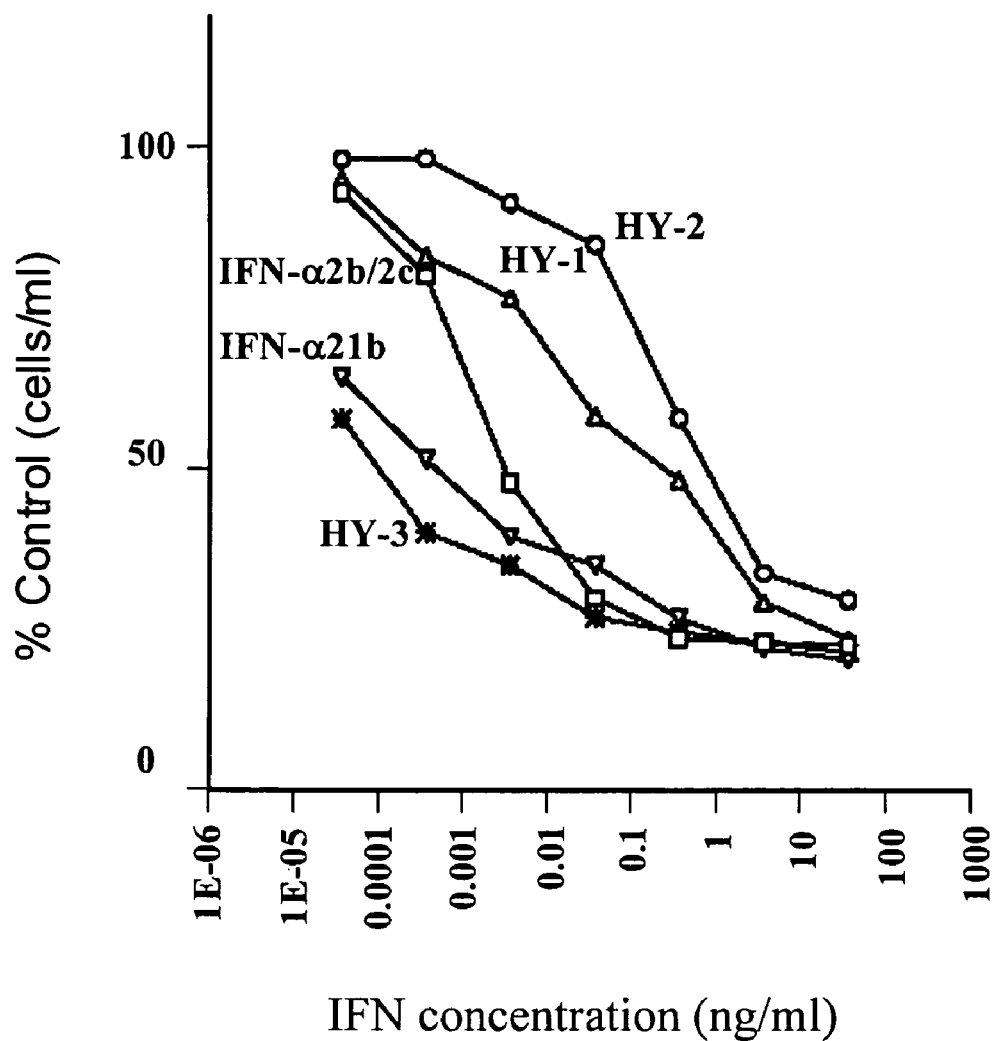
FIG. 2 shows the antiproliferative effects of IFN-α2c (□) and IFN-α21b (∇) compared to that of hybrid IFNs HY-1 (Δ), HY-2 (O) and HY-3 (*). Panel A, Daudi cells, Panel B, WISH cells, and Panel C, primary human lymphocytes.
Figure 2B:
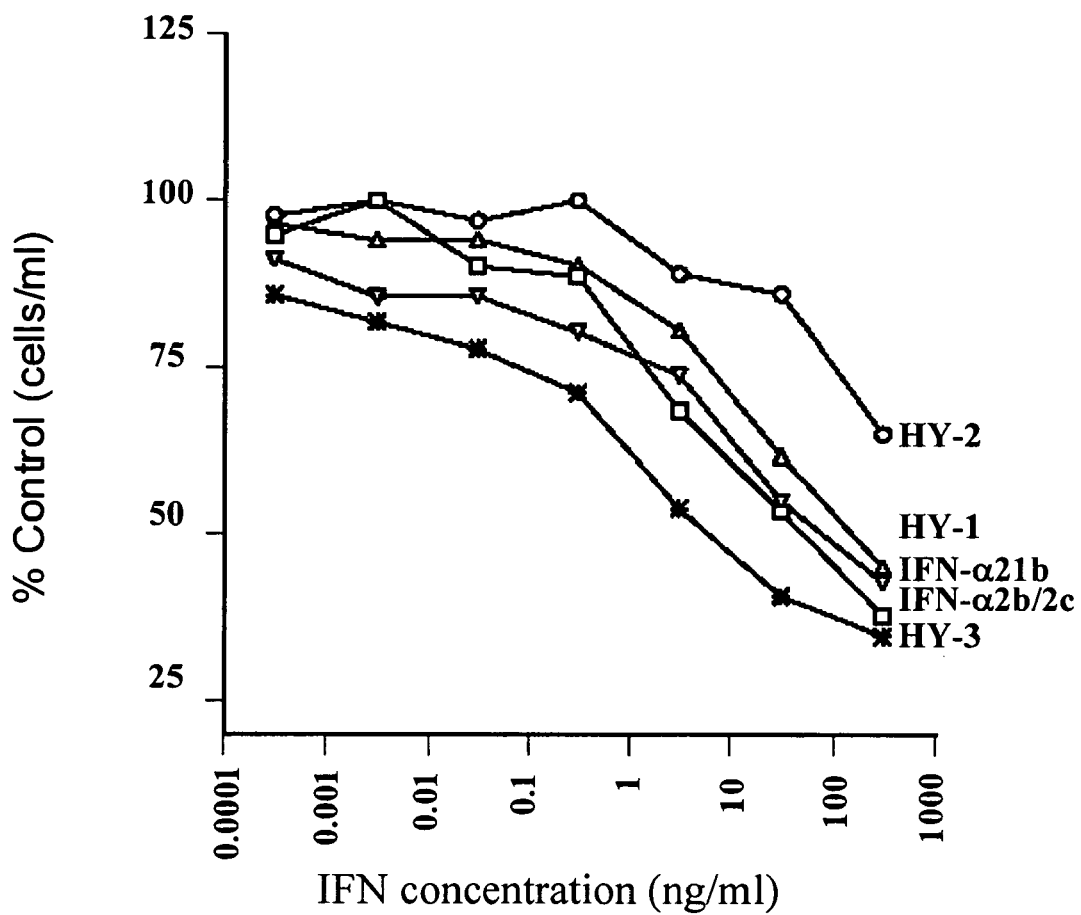
Figure 2C:
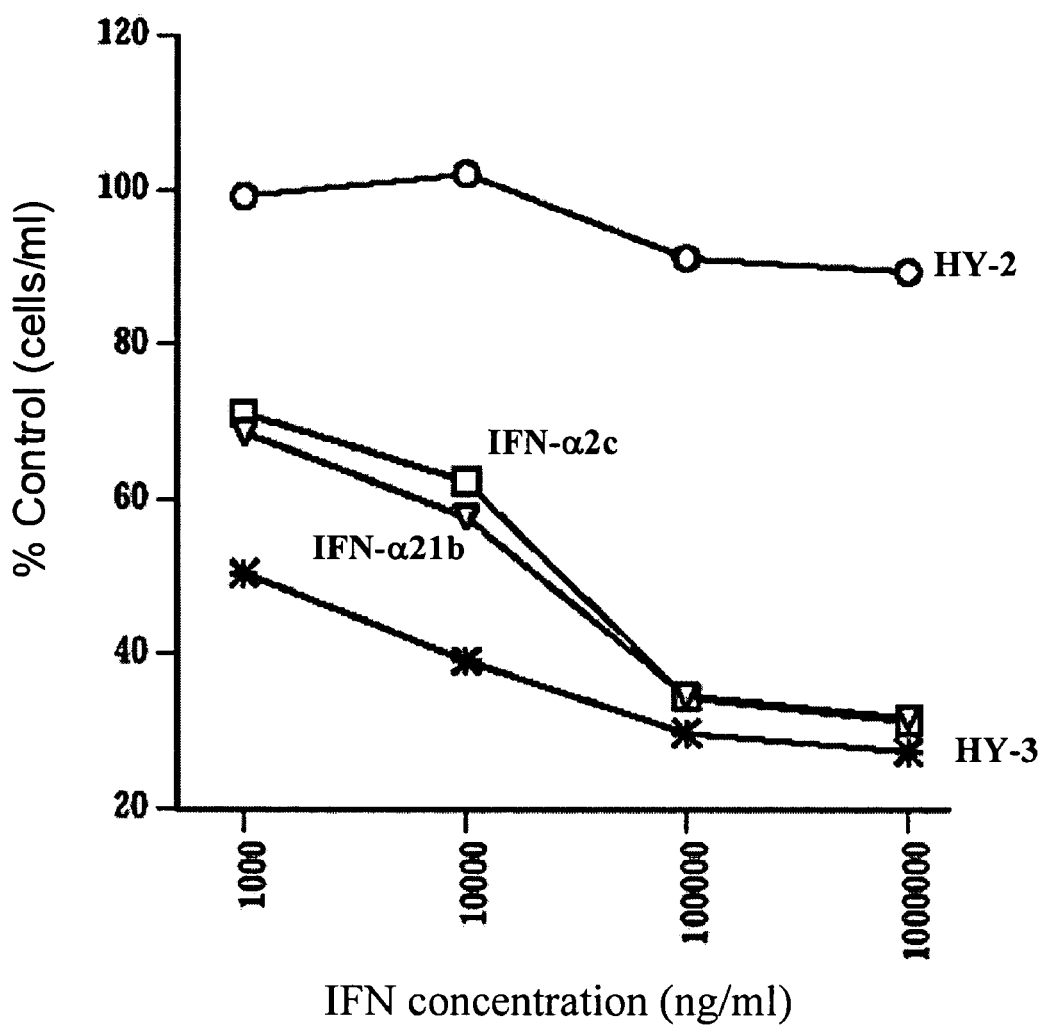

Primary human lymphocytes were treated with phytohemagglutinin (PHA) (Promega) at 1 μg/ml overnight, and the resultant PHA blasts treated for 72 hours with the various IFNs at the concentrations ranging from 0 to 1000 ng/ml. Percent inhibition of proliferation was calculated from direct cell counts, performed by Coulter counter analysis. Results are shown in FIG. 2.

The concentrations of IFN-αs that inhibited Daudi and WISH cell growth by 50% are shown in Table 1. HY-3 exhibited a higher antiproliferative activity than parental interferons IFN-α2c and IFN-α21b and the other hybrids on Daudi, WISH and primary human lymphocyte cells. In comparison, hybrids HY-2 and HY-4 have lower antiproliferative activities than the other hybrids or either of the parental IFN-αs on all these cells. HY-2 displays a 10,000 fold decrease in antiproliferative activity compared to HY-3 on Daudi cells and greater than a 1000 fold decrease on WISH and primary human cells. The hybrid HY-1 has a two- to eight-fold greater antiproliferative activity than HY-2 on Daudi and WISH cells. An intermediate level of antiproliferative activity on Daudi cells was found in the hybrid interferon HY-5 and the two mutant interferon hybrids SDM-1 and SDM-2.

B. Antiviral Activity

The antiviral activities of purified IFN-α hybrids HY-1 through HY-5 and mutant hybrid interferons SDM-1 through SDM-4 were compared to that of parental interferons IFN-α21b and IFN-α2c. MDBK cells (ATCC, Manassas, Va.; ATCC #: CCL-22) were prepared and maintained as described (Zoon et al., 1992). WISH cells were prepared and maintained as above.

Antiviral activity was determined as previously described using MDBK cells and WISH cells (Zoon et al., 1992). All IFN units are expressed with reference to the NIH human lymphoblastoid IFN standard Ga 23-901-532.

The specific antiviral activities on MDBK and WISH cells are shown in Table 1. The antiviral specific activities of the five hybrids and four mutant hybrids are similar to each other and to IFN-α2c and IFN-α21b on MDBK cells ($2.0 \times 10^8$ IU/mg to $5.0 \times 10^8$ IU/mg). The specific activities of HY-1 and HY-2 are seven-fold lower than that of HY-3 on WISH cells.

Figure 3:
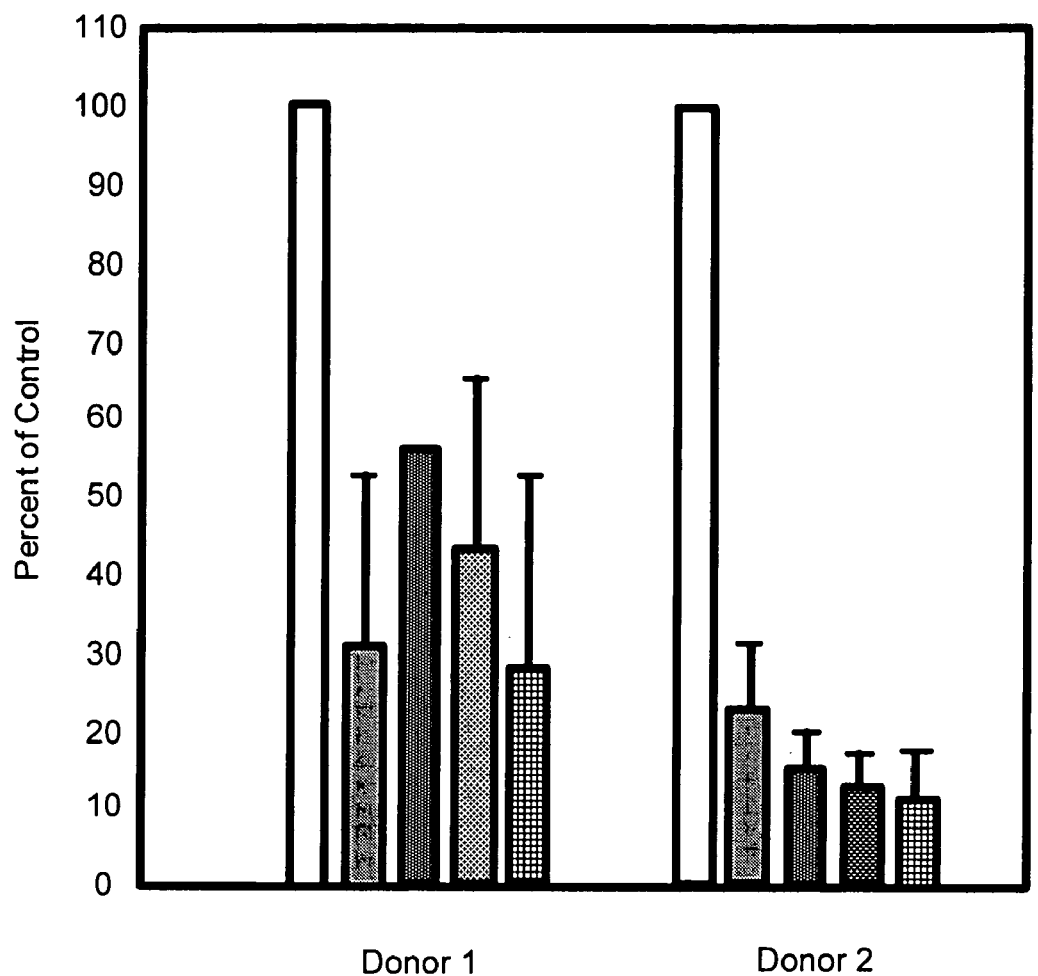
FIG. 3 shows the antiviral activities of IFN-α2c and IFN-α21 b compared to that of hybrid IFNs HY-2 and HY-3 on primary human lymphocytes. Legend: a, No IFN; b, IFN-α2c; c, IFN-α21 b; d, HY-2; e, HY-3.

The Edmonston strain of measles virus (low passage, human embryonic kidney 7, VERO 5) (Albrecht et al., 1981) was plaque-purified and used to infect $1 \times 10^6$ primary human lymphocytes that had been primed for expansion with phytohemagglutinin (PHA). Primary human lymphocytes were obtained from normal donors by centrifugal elutriation after Ficoll-Hypaque sedimentation (Lymphocyte Separation Medium (LSM) Package Insert, ORGANON TEKNIKA, Durham, N.C.). $1 \times 10^8$ cells were resuspended in RPMI-1640 media supplemented with 10% FCS and fungizone (containing penicillin, streptomycin, and amphotericin B) with or without with 100 ng/ml of parental or hybrid interferon for 24 hours prior to infection. These cells were then either infected with measles virus at moi of 0.1-1.6 $TCID_{50}$/ml, or mock infected with virus-free medium, and harvested 72 hours post infection. Supernatants were titrated on VERO cell monolayers. Measles virus cytopathic effect was evaluated microscopically after 6 days and confirmed by staining with crystal violet. FIG. 3 shows the results from lymphocytes from two donors. All experiments were preformed in triplicate and the results are expressed as percent of control; 100 percent for donors 1 and 2 were 4.95 and 5.7 $TCID_{50}$ $log_{10}$, respectively.

C. Interferon Binding

Interferon binding assays were performed as previously described on human Daudi (Hu et al., 1993) and WISH (Zoon et al., 1982) cells. Human IFN-α2b was obtained from Schering Corp. (Kenilworth, N.J.), and has an antiviral specific activity of $2 \times 10^8$ IU/mg protein. IFN-α2b was labeled with $^{125}$I-Bolton-Hunter reagent (Amersham, Arlington Heights, Ill.) as previously described (Hu et al., 1993).

FIG. 4 shows the competitive binding curves for $^{125}$I-labeled IFN-α2b using IFN-α2c, IFN-α21b and the three hybrids (HY-1, HY-2, HY-3) as competitors on Daudi (Panel A) and WISH (Panel B) cells, respectively. The IFN-α2c parent and the hybrid HY-3 compete very well for the $^{125}$I-IFN-α2b binding site on Daudi and WISH cells, while hybrids HY-1 and HY-2, like IFN-α21b, compete poorly for the $^{125}$I-IFN-α2b binding site on Daudi cells. These results are summarized in Table 1.

V. Production of Hybrid Interferon Variants

Of the hybrid IFN-αs herein described, HY-3 has by far the highest antiproliferative activity, exhibiting 1000-10,000-fold higher activity than HY-2 and HY-4. A possible explanation for this high activity is the existence of a domain affecting the antiproliferative activity within the carboxy-region (about residues 76-166) of HY-3. This region comprises a middle element of IFN-α2c (about residues 76-95) fused to the carboxy-terminal element of IFN-α21b (about residues 96-166). One of skill in the art will appreciate that these elements may be combined to produce HY-3-like molecules without necessarily splicing the components in the same place. It might be possible to use shorter or longer fragments of IFN-α2c, fused to correspondingly longer or shorter fragments of IFN-α21b. For instance, the middle element of IFN-α2c might comprise residues 76-96, 76-97 or 76-98, while the carboxy-terminal element of IFN-α21b would correspondingly comprise residues 97-166, 98-166, or 99-166, respectively. Any component that is spliced within 5 amino acid residues of the residue specified comprises about the same region. For instance, amino acid residues 1-80 or 1-70 of IFN-α2c comprise about the same amino acid residues as the component with residues 1-75.

Although in the HY-3 fusion the amino-terminal element of the hybrid comprises amino acid residues 1-75 of IFN-α2c, one skilled in the art will appreciate that other IFN-αs could be used to provide this element. For instance, a HY-3-like polypeptide could be constructed that comprised residues 1-75 of IFN-α21b fused to amino acid residues 76-166 of HY-3. Beyond this, it would be possible to use the amino-terminal element (residues 1-75) of any IFN-α (e.g., IFN-α1, -2, -3, -4, etc.). The designation for a HY-3-like fusion of this type, wherein the amino-terminal 1-75 region comprises amino acids chosen from any IFN-αspecies, is IFN-αX(1-75)/IFN-α2c(76-95)/IFN-α21b(96-166), wherein "IFN-α" designates any IFN-α, including but not limited to IFN-α2c and IFN-α21b. Alternately, such a HY-3-like molecule can be referred to generally as X-A-B, wherein "X" comprises about amino acid residues 1-75 of an interferon-α, "A" comprises about amino acid residues 76-95 of IFN-α2c, and "B" comprises about amino acid residues 96-166 of IFN-α21b. As above, it can be appreciated also that these elements may be spliced in different places. For instance, the amino-terminal element may comprise residues 1-74 or 1-73, fused to amino acid residues 75-166 or 74-166 of HY-3, respectively. Amino-terminal fragments shorter than these could also be employed, with correspondingly longer middle regions. If a parental interferon that has one or more point or short deletions (as found with the 44$^{th}$ position in IFN-α2c) is used in construction of a hybrid, the numbering of the resultant hybrid fusions should be carried out using the facilitated alignment system.

It is further possible that the element that confers increased antiproliferative activity is found wholly within the middle element of IFN-α2c (about residues 76-95). This is supported by the finding that HY-1 has higher antiproliferative activity than HY-2; the sole difference between these two hybrid interferons is the middle element. One skilled in the art will therefore appreciate that another HY-3-like polypeptide could be constructed which comprises an amino-terminal element (about residues 1-75) of any IFN-α, fused to the middle element (about residues 76-95) of IFN-α2c, further fused to the carboxy-terminal element (about residues 96-166) of any IFN-α. In such hybrids, the amino- (about residues 1-75) and carboxy- (about residues 96-166) regions may be provided from any single IFN-α, or from two different IFN-αs. These hybrid IFN molecules are represented as X-A-Y, wherein "X" comprises about amino acid residues 1-75 of any IFN-α, "A" comprises about amino acid residues 76-95 of IFN-α2c, and "Y" comprises about amino acid residues 96-166 of any IFN-α. In addition, as discussed above, the amino- and carboxy-regions may be shorter than those specified herein, for instance amino-regions of 1-74 or 1-73 residues, or carboxy-regions of 97-166 or 96-166. The corresponding middle region of IFN-α2c will vary correspondingly in these latter hybrid molecules. If a parental interferon that has one or more point or short deletions (as found with the 44$^{th}$ position in IFN-α2c) is used in construction of a hybrid, the numbering of the resultant hybrid fusions should be carried out using the facilitated alignment system.

Shorter segments of the IFN-α2c middle region, for instance residues 82-95, are sufficient to confer a substantial portion of the antiproliferative activity found in the HY-3 hybrid. This is evidenced by the high antiproliferative activity of HY-4 (SEQ ID NO: 30). In hybrid constructs using this shorter region of IFN-α2c, the amino- (about residues 1-81) and carboxy- (about residues 96-166) regions may be provided from any single IFN-α, or from two different IFN-αs. Such a hybrid interferon-α molecule with a short IFN-α2c middle region may be represented as V-C-Y, wherein "V" comprises about amino acid residues 1-81 of an interferon-α, "C" comprises about amino acid residues 82-95 of IFN-α2c, and "Y" comprises about amino acid residues 96-166 of an interferon-α. If a parental interferon that has one or more point or short deletions (as found with the 44$^{th}$ position in IFN-α2c) is used in construction of a hybrid, the numbering of the resultant hybrid fusions should be carried out using the facilitated alignment system.

More than three segments or domains of different parental interferons can be used to construct the hybrid IFN-αs of this invention. Such multiple domains are taken from at least two different source or parental interferons, and can be taken from up to as many different interferons as there are fragments assembled to construct the hybrid. A four-domain hybrid interferon-α therefore will be constructed from as few as two or as many as four different interferon-αs. The total length of these constructs will depend on the length(s) of the constituent parental interferons used.

One four domain hybrid interferon-α molecule may be represented as M-N-O-P, wherein "M" comprises about amino acid residues 1-75 of interferon α21b, "N" comprises about amino acid residues 76 to 81 of interferon-α2c, "O" comprises about amino acid residues 82 to 95 of interferon-α 21b, and "P" comprises about amino acid residues 96 to 166 of interferon-α 2c. A representative four domain hybrid interferon of this type is HY-4. If a parental interferon that has one or more point or short deletions (as found with the 44$^{th}$ position in IFN-α2c) is used in construction of a multidomain hybrid, the numbering of the resultant hybrid fusions should be carried out using the facilitated alignment system.

At least a substantial portion of the antiproliferative activity found in HY-3 and the related hybrid and mutant interferons is linked to the presence of either or both of the tyrosine residues found at positions 86 and 90 in the fusion proteins. With the provision herein of the information that these residues are important in interferon biological activity, and specifically antiproliferative activity, this invention also encompasses mutant interferon-αs and mutant hybrid interferon-αs that contain point mutations at either residue 86 or residue 90, thereby changing these residues either to or from a tyrosine. Such point mutations can be introduced into interferon-αs and hybrid interferons through any available mutagenesis techniques, including but not limited to site-directed and PCR mediated mutagenesis. Mutant hybrid interferon polypeptides can for instance contain short or long segments of IFN-α2c, IFN-α21b, or both of these parental interferons. Specific representatives of these mutant hybrid interferons include SDM-1, SDM-2, SDM-3, and SDM-4.

VI. Incorporation of Hybrid and Mutant IFN-αs into Pharmaceutical Compositions

Pharmaceutical compositions that comprise at least one hybrid or mutant hybrid interferon as described herein as an active ingredient will normally be formulated with an appropriate solid or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

Other medicinal and pharmaceutical agents, including non-hybrid interferons, also may be included.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (e.g., syrups, solutions or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art; for example, see Remington's Pharmaceutical Sciences, E. W. Martin, Mack Publishing Co., Easton, Pa., 15th Edition (1975).

The pharmaceutical compositions that comprise hybrid interferon polypeptide will preferably be formulated in unit dosage form, suitable for individual administration of precise dosages. One possible unit dosage contains approximately 100 µg of protein. The amount of active compound administered will be dependent on the subject being treated, the severity of the affliction, and the manner of administration, and is best left to the judgment of the prescribing clinician. Within these bounds, the formulation to be administered will contain a quantity of the active component(s) in an amount effective to achieve the desired effect in the subject being treated.

The herein disclosed hybrid IFNs can also be administered to a patient using other acceptable delivery systems, including liposome-mediated delivery systems as disclosed in WO 96/17596 ("Liposomal interferon hybrid compositions").

The serum half-life of the administered hybrid IFN polypeptide can be extended in various ways, for instance, through formation of a complex with a monoclonal antibody. Such an antibody is usually directed to the hybrid IFN polypeptide at a site that does not materially impair its therapeutic activity (U.S. Pat. No. 5,055,289 "Interferon antibody compositions having an extended serum half-life"). Alternately, interferons can be conjugated to non-antigenic polymers, such as polyethylene glycol or related polyakylene glycol moieties, to increase their serum persistence. See, for instance, Nieforth et al., (1996) and U.S. Pat. Nos. 5,681,811 ("Conjugation-stabilized therapeutic agent compositions, delivery and diagnostic formulations comprising same, and method of making and using same"); 5,711,944 ("Interferon polymer conjugates"); and 5,738,846 ("Interferon polymer conjugates and process for preparing the same").

VII. Clinical Usage of Hybrid and Mutant Hybrid Interferons

The cell growth-regulating activity exhibited by the disclosed hybrid interferons makes these hybrids useful for treating tumors and cancers such as osteogenic sarcoma; multiple myeloma; Hodgkin's disease; nodular, poorly differentiated lymphoma; acute lymphocytic leukemia; acute myeloid leukemia; breast carcinoma; melanoma; papilloma; and nasopharyngeal carcinoma. In addition, the antiviral activity exhibited makes the disclosed hybrid interferons useful for treating viral infections in human and other animal patients. Possibly susceptible virus infections include, but are not limited to, encephalomyocarditis virus infection, influenza and other respiratory tract virus infections, rabies and other viral zoonoses, and arbovirus infections, as well as herpes simplex keratitis, acute hemorrhagic conjunctivitis, varicella zoster, and hepatitis B and C.

The hybrid and mutant hybrid interferons of this invention may be administered to humans, or other animals on whose cells they are effective, in various manners such as topically, orally, intravenously, intramuscularly, intraperitoneally, intranasally, intradermally, intrathecally, and subcutaneously. Administration of hybrid interferon composition is indicated for patients with malignancies or neoplasms, whether or not immunosuppressed, or those patients requiring immunomodulation, or for antiviral treatment. The particular mode of administration and the dosage regimen will be selected by the attending clinician, taking into account the particulars of the case (e.g., the patient, the disease, and the disease state involved). For instance, tumor or cancer treatment typically involves daily or multi-daily doses of hybrid interferon over a period of months or even years. In contrast, viral infections are usually treated by daily doses of hybrid IFN over a few days to weeks. The same dose levels as are used in conventional (non-hybrid) interferon therapy may be used. See U.S. Pat. Nos. 4,089,400 ("Polypeptides and process for the production thereof") and 5,503,828 ("Alpha interferon composition and method for its production from human peripheral blood leukocytes") for general disclosure as to the amounts of IFN-α that have proven efficacious in clinical settings. In general, approximately $10^5$ to $10^8$ IU will be appropriate.

In addition to their individual use, a hybrid and mutant hybrid interferon as disclosed in the current invention may be combined with or used in association with other chemotherapeutic or chemopreventive agents for providing therapy against neoplasms or other conditions against which it is effective. See, for instance, U.S. Pat. No. 4,805,347 ("Interferon combinations"), which discloses various compositions and methods for treating tumors and viruses in humans by administering a combination of IFN-α and an IFN-α2/IFN-α1 hybrid.

The foregoing examples are provided by way of illustration only. One of skill in the art will appreciate that numerous variations on the biological molecules and methods described above may be employed to make and use IFN-α21b/IFN-α2c hybrid interferons. We claim all such subject matter that falls within the scope and spirit of the following claims.

TABLE 1

| Interferon | Antiproliferative Activity (ng/ml)[a] | | | Specific Antiviral Activity (IU/mg) | | | Binding Activity (competes with $^{125}$I-IFN-α2b) (ng/ml)[b] | |
| --- | --- | --- | --- | --- | --- | --- | --- | --- |
| | Daudi Cells | WISH Cells | Ratio WISH/Daudi | MDBK Cells | WISH Cells | Ratio MDBK/WISH | Daudi cells | WISH Cells |
| IFN-α2c | 0.005 | 80 | $1.6 \times 10^4$ | $3.3 \times 10^8$ | $1.9 \times 10^8$ | 1.7 | 35 | 25 |
| IFN-α21a | 0.0008 | 95 | $1.2 \times 10^5$ | $3.7 \times 10^8$ | $0.7 \times 10^8$ | 5.3 | >400 | >200 |
| HY-1 | 0.5 | 110 | $2.2 \times 10^2$ | $2.0 \times 10^8$ | $0.1 \times 10^8$ | 20.0 | >400 | >200 |
| HY-2 | 1.0 | >1000 | $>1 \times 10^3$ | $3.0 \times 10^8$ | $0.1 \times 10^8$ | 30.0 | >400 | >200 |
| HY-3 | 0.0001 | 8 | $8 \times 10^4$ | $2.0 \times 10^8$ | $0.7 \times 10^8$ | 2.9 | 30 | 30 |

TABLE 1-continued

| Interferon | Antiproliferative Activity (ng/ml)[a] | | | Specific Antiviral Activity (IU/mg) | | | Binding Activity (competes with $^{126}$I-IFN-α2b) (ng/ml)[b] | |
|---|---|---|---|---|---|---|---|---|
| | Daudi Cells | WISH Cells | Ratio WISH/ Daudi | MDBK Cells | WISH Cells | Ratio MDBK/WISH | Daudi cells | WISH Cells |
| HY-4 | 1.0 | N/D | | $4.8 \times 10^8$ | N/D | | N/D | N/D |
| HY-5 | 0.03 | NID | | $3.0 \times 10^8$ | N/D | | N/D | N/D |
| SDM-1 | 0.01 | N/D | | $2.7 \times 10^8$ | N/D | | N/D | N/D |
| SDM-2 | 0.013 | N/D | | $4.6 \times 10^8$ | N/D | | N/D | N/D |
| SDM-3 | N/D | N/D | | $4.6 \times 10^8$ | N/D | | N/D | N/D |
| SDM-4 | N/D | N/D | | $5.0 \times 10^8$ | N/D | | N/D | N/D |

[a]Concentration of IFN species that inhibits cell growth by 50%
[b]Concentration of IFN species that inhibits binding of $^{128}$I-IFN-α2b by 50%

REFERENCES

Albrecht et al., (1981) "Role of virus strain in conventional and enhanced measles plaque neutralization test." *J. Virol. Methods* 3(5):251-260.

Allen and Diaz (1996) "Nomenclature of the Human Interferon Proteins." *J. Interferon Res.* 16:181-184.

Ausubel et al., (1987) *In Current Protocols in Molecular Biology*, Greene Publishing Associates and Wiley-Intersciences.

Di Marco et al., (1994) "Mutational analysis of the structure-function relationship in interferon-α." *Biochem. Biophys. Res. Comm.* 202:1445-1451.

*Encyclopedia of Molecular Biology*, published by Blackwell Science Ltd., 1994 (ISBN 0-632-02182-9)

Evinger and Pestka (1981) "Assay of growth inhibition in lymphoblastoid cell cultures." *Methods Enzymol.* 79:362-368.

Fidler et al., (1987) "Direct antiproliferative effects of recombinant human interferon-α B/D hybrids on human tumor cell lines." *Cancer. Res.* 47:2020-2027.

Gresser (1997) "Wherefore interferon?" *J. Leukoc. Biol.* 61(5):567-574.

Grander et al., (1997) "How does interferon exert its cell growth inhibitory effect?" *Eur. J. Haematol.* 59:129-135.

Hayes and Zoon (1993) "Priming of Human Monocytes for enhanced lipopolysaccharide responses: Expression of alpha interferon, interferon regulatory factors, and tumor necrosis factor." *Infect. Immun.* 61:3222-3227.

Horisberger and Di Marco (1995) "Interferon-alpha hybrids." *Pharmac. Ther.* 55:507-534.

Horton et al., (1989) "Engineering hybrid genes without the use of restriction enzymes." *Gene* 77:61-68.

Hu et al., (1993) "Evidence for multiple binding sites for several components of human lymphoblastoid interferon-α." *J. Biol. Chem.* 268:12591-12595.

Innis et al., (eds.) (1990) "*PCR Protocols, A Guide to Methods and Applications*." Academic Press, Inc., San Diego, Calif.

Janknecht et al., (1991) "Rapid and efficient purification of native, histidine-tagged protein expressed by recombinant vaccinia virus." *Proc. Natl. Acad. Sci. USA* 88:8972-8976.

Joshua et al., (1997) "Role of alpha interferon in multiple myeloma." *Blood Rev.* 11(4):191-200.

Lewin, B., *Genes V* published by Oxford University Press, 1994 (ISBN 0-19-854287-9); Kendrew et al., (Eds.).

McNeill (1981) "Interferon assay." *J. Immunological Methods* 46:121-127.

Meister et al., (1986) "Biological activities and receptor binding of two human recombinant interferons and their hybrids." *L. Gen. Virol.* 67:1633-1643.

Meyers (Ed.), *Molecular Biology and Biotechnology: a Comprehensive Desk Reference*, published by VCH Publishers, Inc., 1995 (ISBN 1-56081-569-8)

Mitsui et al., (1993) "Structural, functional and evolutionary implications of the three-dimensional crystal structure of murine interferon-α." *Pharmac. Ther.* 58:93-132.

Moussalli et al., (1998) "Management of hepatitis C." *J. Viral. Hepat.* 5(2):73-82.

Muller et al., (1994) "Functional role of type I and type II interferons in antiviral defense." *Science* 264:1918-1921.

Neiforth, et al., (1996) "Use of an indirect pharmacodynamic stimulation model of MX protein induction to compare in vivo activity of interferon alfa-2a and a polyethylene glycol-modified derivative in healthy subjects." *Clin. Pharmacol. Ther.* 59(6):636-646.

Pfeffer (1997) "Biologic activities of natural and synthetic type I interferons." *Semin. Oncol.* 24(3 Suppl. 9):S9-S63S969.

*The QIA expressionist: The high level expression and protein purification system.* (1997) (Handbook). QIAGEN, Chatsworth, Calif.

Rehberg et al., (1982) "Specific molecular activities of recombinant and hybrid leukocyte interferons." *J. Biol. Chem.* 257:11497-11502.

Rubinstein et al., (1981) "Convenient assay for interferon." *J. Virol.* 37:755-758.

Sambrook et al., (1989) *In Molecular Cloning: A Laboratory Manual*, Cold Spring Harbor, N. Y.

Sanger et al., (1977) "DNA sequencing with chain-terminating inhibitors." *Proc. Natl. Acad. Sci. USA* 74:5463-5467.

Sperber et al., (1993) "Anti-rhinoviral activity of recombinant and hybrid species of interferon alpha." *Antiviral Res.* 22:121-129.

Streuli et al., (1981) "Target-cell specificity of two species of human interferon-α produced in *E. coli* and of hybrid molecules derived from them." *Proc. Natl. Acad. Sci.* 78:2848-2852.

Tilg (1997) "New insights into the mechanisms of interferon alfa: an immunoregulatory and anti-inflammatory cytokine." *Gastroenterology.* 112(3): 1017-1021.

Williams and Linch (1997) "Interferon alfa-2a." *Br. J. Hosp. Med.* 57(9):436-439.

Zav'Yalov and Zav'Yalov (1997) "Interferons alpha/beta and their receptors: Place in the hierarchy of cytokines." APMIS 105:161-186.

Zoon et al., (1982) "Specific binding of human α-interferon to a high affinity cell surface binding site on Bovine Kidney Cells." *J. Biol. Chem.* 257:4695-4697.

Zoon et al., (1986) "Chemical and biological characterization of natural human lymphoblastoid interferon alphas." In, *The Biology of the Interferon System*. Cantell and Schellenkens, Eds., Martinus Nyhoff Publishers, Amsterdam.

Zoon et al., (1992) "Purification and characterization of multiple components of human lymphoblastoid interferon-α." *J. Biol. Chem.* 267:15210-15219.

```
                              SEQUENCE LISTING

<160> NUMBER OF SEQ ID NOS: 42

<210> SEQ ID NO 1
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 1
tccggatcct gtgatctgcc tcagacc                                         27

<210> SEQ ID NO 2
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 2
agcagatgag tcctttgtgc tgaagag                                         27

<210> SEQ ID NO 3
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 3
ctcttcagca caaaggactc atctgct                                         27

<210> SEQ ID NO 4
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 4
gagctcgcat gctcatcatt ccttacttct taaact                               36

<210> SEQ ID NO 5
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 5
cacgcaggcc tcgaggtcat tcag                                            24

<210> SEQ ID NO 6
<211> LENGTH: 24
<212> TYPE: DNA
```

```
<213> ORGANISM: Artificial Sequence
<220> FEATURE:
<223> OTHER INFORMATION: Synthetic Oligonucleotide

<400> SEQUENCE: 6
ctgaatgacc tcgaggcctg cgtg                                          24

<210> SEQ ID NO 7
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 7
gagctcgcat gctcatcatt ccttcctcct taatct                             36

<210> SEQ ID NO 8
<211> LENGTH: 500
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(498)

<400> SEQUENCE: 8 tgt gat ctg cct cag acc cac agc ctg ggt aat agg agg gcc ttg ata     48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac     96
Leu Leu Ala Gln Met Gly Arg Ile Ser Pro Phe Ser Cys Leu Lys Asp
            20                  25                  30 aga cat gac ttt gga ttc ccc caa gag gag ttt gat ggc aac cag ttc    144
Arg His Asp Phe Gly Phe Pro Gln Glu Glu Phe Asp Gly Asn Gln Phe
        35                  40                  45 cag aag gct caa gcc atc tct gtc ctc cat gag atg atc cag cag acc    192
Gln Lys Ala Gln Ala Ile Ser Val Leu His Glu Met Ile Gln Gln Thr
    50                  55                  60 ttc aat ctc ttc agc aca aag gac tca tct gct gct tgg gat gag acc    240
Phe Asn Leu Phe Ser Thr Lys Asp Ser Ser Ala Ala Trp Asp Glu Thr
65                  70                  75                  80 ctc cta gac aaa ttc tac act gaa ctc tac cag cag ctg aat gac ctg    288
Leu Leu Asp Lys Phe Tyr Thr Glu Leu Tyr Gln Gln Leu Asn Asp Leu
                85                  90                  95 gaa gcc tgt gtg ata cag ggg gtg ggg gtg aca gag act ccc ctg atg    336
Glu Ala Cys Val Ile Gln Gly Val Gly Val Thr Glu Thr Pro Leu Met
            100                 105                 110 aag gag gac tcc att ctg gct gtg agg aaa tac ttc caa aga atc act    384
Lys Glu Asp Ser Ile Leu Ala Val Arg Lys Tyr Phe Gln Arg Ile Thr
        115                 120                 125 ctc tat ctg aaa gag aag aaa tac agc cct tgt gcc tgg gag gtt gtc    432
Leu Tyr Leu Lys Glu Lys Lys Tyr Ser Pro Cys Ala Trp Glu Val Val
    130                 135                 140 aga gca gaa atc atg aga tct ttt tct ttg tca aca aac ttg caa gaa    480
Arg Ala Glu Ile Met Arg Ser Phe Ser Leu Ser Thr Asn Leu Gln Glu
145                 150                 155                 160 agt tta aga agt aag gaa tg                                         500
Ser Leu Arg Ser Lys Glu
                165

<210> SEQ ID NO 9
```

<211> LENGTH: 166
<212> TYPE: PRT
<213> ORGANISM: Artificial Sequence
<220> FEATURE:
<223> OTHER INFORMATION: Gene Fusion

<400> SEQUENCE: 9

```
Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165
```

<210> SEQ ID NO 10
<211> LENGTH: 500
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(498)

<400> SEQUENCE: 10

```
tgt gat ctg cct cag acc cac agc ctg ggt aat agg agg gcc ttg ata      48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac      96
Leu Leu Ala Gln Met Gly Arg Ile Ser Pro Phe Ser Cys Leu Lys Asp
            20                  25                  30 aga cat gac ttt gga ttc ccc cag gag gag ttt gat ggc aac cag ttc     144
Arg His Asp Phe Gly Phe Pro Gln Glu Glu Phe Asp Gly Asn Gln Phe
        35                  40                  45 cag aag gct caa gcc atc tct gtc ctc cat gag atg atc cag cag acc     192
Gln Lys Ala Gln Ala Ile Ser Val Leu His Glu Met Ile Gln Gln Thr
    50                  55                  60 ttc aat ctc ttc agc aca aag gac tca tct gct act tgg gaa cag agc     240
Phe Asn Leu Phe Ser Thr Lys Asp Ser Ser Ala Thr Trp Glu Gln Ser
65                  70                  75                  80 ctc cta gaa aaa ttt tcc act gaa ctt aac cag cag ctg aat gac ctc     288
Leu Leu Glu Lys Phe Ser Thr Glu Leu Asn Gln Gln Leu Asn Asp Leu
                85                  90                  95 gag gcc tgt gtg ata cag ggg gtg ggg gtg aca gag act ccc ctg atg    336
Glu Ala Cys Val Ile Gln Gly Val Gly Val Thr Glu Thr Pro Leu Met
```

```
                Glu Ala Cys Val Ile Gln Gly Val Gly Val Thr Glu Thr Pro Leu Met
                                100                 105                 110 aag gag gac tcc att ctg gct gtg agg aaa tac ttc caa aga atc act      384
                Lys Glu Asp Ser Ile Leu Ala Val Arg Lys Tyr Phe Gln Arg Ile Thr
                            115                 120                 125 ctc tat ctg aaa gag aag aaa tac agc cct tgt gcc tgg gaa gtt gtc      432
                Leu Tyr Leu Lys Glu Lys Lys Tyr Ser Pro Cys Ala Trp Glu Val Val
                        130                 135                 140 aga gca gaa atc atg aga tct ttt tct ttg tca aca aac ttg caa gaa      480
                Arg Ala Glu Ile Met Arg Ser Phe Ser Leu Ser Thr Asn Leu Gln Glu
                145                 150                 155                 160 agt tta aga agt aag gaa tg                                           500
                Ser Leu Arg Ser Lys Glu
                                165

<210> SEQ ID NO 11
<211> LENGTH: 166
<212> TYPE: PRT
<213> ORGANISM: Artificial Sequence
<220> FEATURE:
<223> OTHER INFORMATION: Gene Fusion

<400> SEQUENCE: 11

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 12
<211> LENGTH: 497
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(495)

<400> SEQUENCE: 12 tgt gat ctg cct cag acc cac agc ctg ggt agc agg agg acc ttg atg      48
                Cys Asp Leu Pro Gln Thr His Ser Leu Gly Ser Arg Arg Thr Leu Met
                1               5                   10                  15
```

```
ctc ctg gca cag atg agg aga atc tct ctt ttc tcc tgc ttg aag gac    96
Leu Leu Ala Gln Met Arg Arg Ile Ser Leu Phe Ser Cys Leu Lys Asp
         20                  25                  30 aga cgt gac ttt gga ttt ccc cag gag gag ttt ggc aac cag ttc caa    144
Arg Arg Asp Phe Gly Phe Pro Gln Glu Glu Phe Gly Asn Gln Phe Gln
             35                  40                  45 aag gct gaa acc atc cct gtc ctc cat gag atg atc cag cag atc ttc    192
Lys Ala Glu Thr Ile Pro Val Leu His Glu Met Ile Gln Gln Ile Phe
 50                  55                  60 aat ctc ttc agc aca aag gac tca tct gct gct tgg gat gag acc ctc    240
Asn Leu Phe Ser Thr Lys Asp Ser Ser Ala Ala Trp Asp Glu Thr Leu
 65                  70                  75                  80 cta gac aaa ttc tac act gaa ctc tac cag cag ctg aat gac ctc gag    288
Leu Asp Lys Phe Tyr Thr Glu Leu Tyr Gln Gln Leu Asn Asp Leu Glu
                 85                  90                  95 gcc tgc gtg ata cag gag gtt ggg gtg gaa gag act ccc ctg atg aat    336
Ala Cys Val Ile Gln Glu Val Gly Val Glu Glu Thr Pro Leu Met Asn
                100                 105                 110 gtg gac tcc atc ctg gct gtg aag aaa tac ttc caa aga atc act ctt    384
Val Asp Ser Ile Leu Ala Val Lys Lys Tyr Phe Gln Arg Ile Thr Leu
            115                 120                 125 tat ctg aca gag aag aaa tac agc cct tgt gcc tgg gag gtt gtc aga    432
Tyr Leu Thr Glu Lys Lys Tyr Ser Pro Cys Ala Trp Glu Val Val Arg
        130                 135                 140 gca gaa atc atg aga tcc ttc tct tta tca aaa att ttt caa gaa aga    480
Ala Glu Ile Met Arg Ser Phe Ser Leu Ser Lys Ile Phe Gln Glu Arg
145                 150                 155                 160 tta agg agg aag gaa tg                                             497
Leu Arg Arg Lys Glu
                165
```

<210> SEQ ID NO 13
<211> LENGTH: 165
<212> TYPE: PRT
<213> ORGANISM: Artificial Sequence
<220> FEATURE:
<223> OTHER INFORMATION: Gene Fusion

<400> SEQUENCE: 13

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg Arg Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
 50                 55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Glu Val Gly Val Glu Glu Thr Pro Leu Met Asn
            100                 105                 110

Val Asp Ser Ile Leu Ala Val Lys Lys Tyr Phe Gln Arg Ile Thr Leu
        115                 120                 125

Tyr Leu Thr Glu Lys Lys Tyr Ser Pro Cys Ala Trp Glu Val Val Arg
    130                 135                 140

Ala Glu Ile Met Arg Ser Phe Ser Leu Ser Lys Ile Phe Gln Glu Arg
145                 150                 155                 160
```

Leu Arg Arg Lys Glu
            165

<210> SEQ ID NO 14
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 14
gctgcttggg atgagaccct ccta                                    24

<210> SEQ ID NO 15
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 15
taggagggtc tcatcccaag cagc                                    24

<210> SEQ ID NO 16
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 16
ctagacaaat tctacactga actctaccag                              30

<210> SEQ ID NO 17
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 17
ctggtagagt tcagtgtaga atttgtctag                              30

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 18
ctgaatgacc tcgaggcctg cgtg                                    24

<210> SEQ ID NO 19
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 19
cacgcaggcc tcgaggtcat tcag                                    24

<210> SEQ ID NO 20
<211> LENGTH: 21

<212> TYPE: DNA
<213> ORGANISM: Artificial Sequence
<220> FEATURE:
<223> OTHER INFORMATION: Synthetic Oligonucleotide

<400> SEQUENCE: 20
gaaaaatttt acactgaact t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 21
aagttcagtg taaaattttt c                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 22
actgaacttt accagcagct g                                              21

<210> SEQ ID NO 23
<211> LENGTH: 21
<212> TYPE: DNA
<213> ORGANISM: Artificial Sequence
<220> FEATURE:
<223> OTHER INFORMATION: Synethetic Oligonucleotide

<400> SEQUENCE: 23
cagctgctgg taaagttcag t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 24
gacaaattct ccactgaact c                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 25
gagttcagtg gagaatttgt c                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 26

```
actgaactca accagcagct g                                              21
```

<210> SEQ ID NO 27
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 27

```
cagctgctgg ttgagttcag t                                              21
```

<210> SEQ ID NO 28
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 28

```
gagctcgcat gctcatcatt ccttacttct taaact                              36
```

<210> SEQ ID NO 29
<211> LENGTH: 500
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(498)

<400> SEQUENCE: 29

```
tgt gat ctg cct cag acc cac agc ctg ggt aat agg agg gcc ttg ata      48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac      96
Leu Leu Ala Gln Met Gly Arg Ile Ser Pro Phe Ser Cys Leu Lys Asp
                20                  25                  30 aga cat gac ttt gga ttc ccc cag gag gag ttt gat ggc aac cag ttc     144
Arg His Asp Phe Gly Phe Pro Gln Glu Glu Phe Asp Gly Asn Gln Phe
            35                  40                  45 cag aag gct caa gcc atc tct gtc ctc cat gag atg atc cag cag acc     192
Gln Lys Ala Gln Ala Ile Ser Val Leu His Glu Met Ile Gln Gln Thr
        50                  55                  60 ttc aat ctc ttc agc aca aag gac tca tct gct gct tgg gat gag acc     240
Phe Asn Leu Phe Ser Thr Lys Asp Ser Ser Ala Ala Trp Asp Glu Thr
65                  70                  75                  80 ctc cta gaa aaa ttt tcc act gaa ctt aac cag cag ctg aat gac ctc     288
Leu Leu Glu Lys Phe Ser Thr Glu Leu Asn Gln Gln Leu Asn Asp Leu
                85                  90                  95 gag gcc tgt gtg ata cag ggg gtg ggg gtg aca gag act ccc ctg atg     336
Glu Ala Cys Val Ile Gln Gly Val Gly Val Thr Glu Thr Pro Leu Met
                100                 105                 110 aag gag gac tcc att ctg gct gtg agg aaa tac ttc caa aga atc act     384
Lys Glu Asp Ser Ile Leu Ala Val Arg Lys Tyr Phe Gln Arg Ile Thr
            115                 120                 125 ctc tat ctg aaa gag aag aaa tac agc cct tgt gcc tgg gag gtt gtc     432
Leu Tyr Leu Lys Glu Lys Lys Tyr Ser Pro Cys Ala Trp Glu Val Val
        130                 135                 140 aga gca gaa atc atg aga tct ttt tct ttg tca aca aac ttg caa gaa     480
Arg Ala Glu Ile Met Arg Ser Phe Ser Leu Ser Thr Asn Leu Gln Glu
145                 150                 155                 160
```

```
agt tta aga agt aag gaa tg                                          500
Ser Leu Arg Ser Lys Glu
            165

<210> SEQ ID NO 30
<211> LENGTH: 166
<212> TYPE: PRT
<213> ORGANISM: Artificial Sequence
<220> FEATURE:
<223> OTHER INFORMATION: Gene Fusion

<400> SEQUENCE: 30

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Ser Thr Glu Leu Asn Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
            165

<210> SEQ ID NO 31
<211> LENGTH: 500
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(498)

<400> SEQUENCE: 31 tgt gat ctg cct cag acc cac agc ctg ggt aat agg agg gcc ttg ata    48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac    96
Leu Leu Ala Gln Met Gly Arg Ile Ser Pro Phe Ser Cys Leu Lys Asp
            20                  25                  30 aga cat gac ttt gga ttc ccc cag gag gag ttt gat ggc aac cag ttc   144
Arg His Asp Phe Gly Phe Pro Gln Glu Glu Phe Asp Gly Asn Gln Phe
        35                  40                  45 cag aag gct caa gcc atc tct gtc ctc cat gag atg atc cag cag acc   192
Gln Lys Ala Gln Ala Ile Ser Val Leu His Glu Met Ile Gln Gln Thr
    50                  55                  60 ttc aat ctc ttc agc aca aag gac tca tct gct act tgg gaa cag agc   240
Phe Asn Leu Phe Ser Thr Lys Asp Ser Ser Ala Thr Trp Glu Gln Ser
65                  70                  75                  80
```

```
ctc cta gac aaa ttc tac act gaa ctc tac cag cag ctg aat gac ctc      288
Leu Leu Asp Lys Phe Tyr Thr Glu Leu Tyr Gln Gln Leu Asn Asp Leu
            85                  90                  95 gag gcc tgt gtg ata cag ggg gtg ggg gtg aca gag act ccc ctg atg      336
Glu Ala Cys Val Ile Gln Gly Val Gly Val Thr Glu Thr Pro Leu Met
        100                 105                 110 aag gag gac tcc att ctg gct gtg agg aaa tac ttc caa aga atc act      384
Lys Glu Asp Ser Ile Leu Ala Val Arg Lys Tyr Phe Gln Arg Ile Thr
                115                 120                 125 ctc tat ctg aaa gag aag aaa tac agc cct tgt gcc tgg gag gtt gtc      432
Leu Tyr Leu Lys Glu Lys Lys Tyr Ser Pro Cys Ala Trp Glu Val Val
    130                 135                 140 aga gca gaa atc atg aga tct ttt tct ttg tca aca aac ttg caa gaa      480
Arg Ala Glu Ile Met Arg Ser Phe Ser Leu Ser Thr Asn Leu Gln Glu
145                 150                 155                 160 agt tta aga agt aag gaa tg                                           500
Ser Leu Arg Ser Lys Glu
                165

<210> SEQ ID NO 32
<211> LENGTH: 166
<212> TYPE: PRT
<213> ORGANISM: Artificial Sequence
<220> FEATURE:
<223> OTHER INFORMATION: Gene Fusion

<400> SEQUENCE: 32

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Asp Lys Phe Tyr Thr Glu Leu Tyr Gln Gln Leu Asn Asp Leu
            85                  90                  95

Glu Ala Cys Val Ile Gln Gly Val Gly Val Thr Glu Thr Pro Leu Met
        100                 105                 110

Lys Glu Asp Ser Ile Leu Ala Val Arg Lys Tyr Phe Gln Arg Ile Thr
    115                 120                 125

Leu Tyr Leu Lys Glu Lys Lys Tyr Ser Pro Cys Ala Trp Glu Val Val
130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 33
<211> LENGTH: 500
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(498)
```

```
<400> SEQUENCE: 33 tgt gat ctg cct cag acc cac agc ctg ggt aat agg agg gcc ttg ata      48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac      96
Leu Leu Ala Gln Met Gly Arg Ile Ser Pro Phe Ser Cys Leu Lys Asp
            20                  25                  30 aga cat gac ttt gga ttc ccc caa gag gag ttt gat ggc aac cag ttc     144
Arg His Asp Phe Gly Phe Pro Gln Glu Glu Phe Asp Gly Asn Gln Phe
        35                  40                  45 cag aag gct caa gcc atc tct gtc ctc cat gag atg atc cag cag acc     192
Gln Lys Ala Gln Ala Ile Ser Val Leu His Glu Met Ile Gln Gln Thr
    50                  55                  60 ttc aat ctc ttc agc aca aag gac tca tct gct gct tgg gat gag acc     240
Phe Asn Leu Phe Ser Thr Lys Asp Ser Ser Ala Ala Trp Asp Glu Thr
65                  70                  75                  80 ctc cta gac aaa ttc tac act gaa ctc tac cag cag ctg aat gac ctg     288
Leu Leu Asp Lys Phe Tyr Thr Glu Leu Tyr Gln Gln Leu Asn Asp Leu
                85                  90                  95 gaa gcc tgc gtg ata cag gag gtt ggg gtg gaa gag act ccc ctg atg     336
Glu Ala Cys Val Ile Gln Glu Val Gly Val Glu Glu Thr Pro Leu Met
            100                 105                 110 aat gtg gac tcc atc ttg gct gtg aag aaa tac ttc caa aga atc act     384
Asn Val Asp Ser Ile Leu Ala Val Lys Lys Tyr Phe Gln Arg Ile Thr
        115                 120                 125 ctt tat ctg aca gag aag aaa tac agc cct tgt gct tgg gag gtt gtc     432
Leu Tyr Leu Thr Glu Lys Lys Tyr Ser Pro Cys Ala Trp Glu Val Val
    130                 135                 140 aga gca gaa atc atg aga tcc ttc tct tta tca aaa att ttt caa gaa     480
Arg Ala Glu Ile Met Arg Ser Phe Ser Leu Ser Lys Ile Phe Gln Glu
145                 150                 155                 160 aga tta agg agg aag gaa tg                                          500
Arg Leu Arg Arg Lys Glu
                165

<210> SEQ ID NO 34
<211> LENGTH: 166
<212> TYPE: PRT
<213> ORGANISM: Artificial Sequence
<220> FEATURE:
<223> OTHER INFORMATION: Gene Fusion

<400> SEQUENCE: 34

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Lys Lys Tyr Phe Gln Arg Ile Thr
        115                 120                 125
```

```
Leu Tyr Leu Thr Glu Lys Lys Tyr Ser Pro Cys Ala Trp Glu Val Val
    130                 135                 140

Arg Ala Glu Ile Met Arg Ser Phe Ser Leu Ser Lys Ile Phe Gln Glu
145                 150                 155                 160

Arg Leu Arg Arg Lys Glu
                165

<210> SEQ ID NO 35
<211> LENGTH: 500
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(498)

<400> SEQUENCE: 35 tgt gat ctg cct cag acc cac agc ctg ggt aat agg agg gcc ttg ata      48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac      96
Leu Leu Ala Gln Met Gly Arg Ile Ser Pro Phe Ser Cys Leu Lys Asp
            20                  25                  30 aga cat gac ttt gga ttc ccc cag gag gag ttt gat ggc aac cag ttc     144
Arg His Asp Phe Gly Phe Pro Gln Glu Glu Phe Asp Gly Asn Gln Phe
        35                  40                  45 cag aag gct caa gcc atc tct gtc ctc cat gag atg atc cag cag acc     192
Gln Lys Ala Gln Ala Ile Ser Val Leu His Glu Met Ile Gln Gln Thr
    50                  55                  60 ttc aat ctc ttc agc aca aag gac tca tct gct gct tgg gat gag acc     240
Phe Asn Leu Phe Ser Thr Lys Asp Ser Ser Ala Ala Trp Asp Glu Thr
65                  70                  75                  80 ctc cta gaa aaa ttt tac act gaa ctt aac cag cag ctg aat gac ctc     288
Leu Leu Glu Lys Phe Tyr Thr Glu Leu Asn Gln Gln Leu Asn Asp Leu
                85                  90                  95 gag gcc tgt gtg ata cag ggg gtg ggg gtg aca gag act ccc ctg atg     336
Glu Ala Cys Val Ile Gln Gly Val Gly Val Thr Glu Thr Pro Leu Met
            100                 105                 110 aag gag gac tcc att ctg gct gtg agg aaa tac ttc caa aga atc act     384
Lys Glu Asp Ser Ile Leu Ala Val Arg Lys Tyr Phe Gln Arg Ile Thr
        115                 120                 125 ctc tat ctg aaa gag aag aaa tac agc cct tgt gcc tgg gag gtt gtc     432
Leu Tyr Leu Lys Glu Lys Lys Tyr Ser Pro Cys Ala Trp Glu Val Val
    130                 135                 140 aga gca gaa atc atg aga tct ttt tct ttg tca aca aac ttg caa gaa     480
Arg Ala Glu Ile Met Arg Ser Phe Ser Leu Ser Thr Asn Leu Gln Glu
145                 150                 155                 160 agt tta aga agt aag gaa tg                                          500
Ser Leu Arg Ser Lys Glu
                165

<210> SEQ ID NO 36
<211> LENGTH: 166
<212> TYPE: PRT
<213> ORGANISM: Artificial Sequence
<220> FEATURE:
<223> OTHER INFORMATION: Gene Fusion

<400> SEQUENCE: 36

Cys Asp Leu Pro Gln Thr His Ser Leu Gly Asn Arg Arg Ala Leu Ile
1               5                   10                  15
```

```
Leu Leu Ala Gln Met Gly Arg Ile Ser Pro Phe Ser Cys Leu Lys Asp
             20                  25                  30

Arg His Asp Phe Gly Phe Pro Gln Glu Glu Phe Asp Gly Asn Gln Phe
         35                  40                  45

Gln Lys Ala Gln Ala Ile Ser Val Leu His Glu Met Ile Gln Gln Thr
     50                  55                  60

Phe Asn Leu Phe Ser Thr Lys Asp Ser Ser Ala Ala Trp Asp Glu Thr
 65                  70                  75                  80

Leu Leu Glu Lys Phe Tyr Thr Glu Leu Asn Gln Gln Leu Asn Asp Leu
                 85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
            115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 37
<211> LENGTH: 500
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(498)

<400> SEQUENCE: 37 tgt gat ctg cct cag acc cac agc ctg ggt aat agg agg gcc ttg ata      48
Cys Asp Leu Pro Gln Thr His Ser Leu Gly Asn Arg Arg Ala Leu Ile
  1               5                  10                  15 ctc ctg gca caa atg gga aga atc tct cct ttc tcc tgc ctg aag gac      96
Leu Leu Ala Gln Met Gly Arg Ile Ser Pro Phe Ser Cys Leu Lys Asp
             20                  25                  30 aga cat gac ttt gga ttc ccc cag gag gag ttt gat ggc aac cag ttc     144
Arg His Asp Phe Gly Phe Pro Gln Glu Glu Phe Asp Gly Asn Gln Phe
         35                  40                  45 cag aag gct caa gcc atc tct gtc ctc cat gag atg atc cag cag acc     192
Gln Lys Ala Gln Ala Ile Ser Val Leu His Glu Met Ile Gln Gln Thr
     50                  55                  60 ttc aat ctc ttc agc aca aag gac tca tct gct gct tgg gat gag acc     240
Phe Asn Leu Phe Ser Thr Lys Asp Ser Ser Ala Ala Trp Asp Glu Thr
 65                  70                  75                  80 ctc cta gaa aaa ttt tcc act gaa ctt tac cag cag ctg aat gac ctc     288
Leu Leu Glu Lys Phe Ser Thr Glu Leu Tyr Gln Gln Leu Asn Asp Leu
                 85                  90                  95 gag gcc tgt gtg ata cag ggg gtg ggg gtg aca gag act ccc ctg atg     336
Glu Ala Cys Val Ile Gln Gly Val Gly Val Thr Glu Thr Pro Leu Met
            100                 105                 110 aag gag gac tcc att ctg gct gtg agg aaa tac ttc caa aga atc act     384
Lys Glu Asp Ser Ile Leu Ala Val Arg Lys Tyr Phe Gln Arg Ile Thr
            115                 120                 125 ctc tat ctg aaa gag aag aaa tac agc cct tgt gcc tgg gag gtt gtc     432
Leu Tyr Leu Lys Glu Lys Lys Tyr Ser Pro Cys Ala Trp Glu Val Val
    130                 135                 140
```

```
aga gca gaa atc atg aga tct ttt tct ttg tca aca aac ttg caa gaa    480
Arg Ala Glu Ile Met Arg Ser Phe Ser Leu Ser Thr Asn Leu Gln Glu
145                 150                 155                 160 agt tta aga agt aag gaa tg                                          500
Ser Leu Arg Ser Lys Glu
            165
```

<210> SEQ ID NO 38
<211> LENGTH: 166
<212> TYPE: PRT
<213> ORGANISM: Artificial Sequence
<220> FEATURE:
<223> OTHER INFORMATION: Gene Fusion

<400> SEQUENCE: 38

```
Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Trp Asp Glu Thr
65                  70                  75                  80

Leu Leu Glu Lys Phe Ser Thr Glu Leu Tyr Gln Gln Leu Asn Asp Leu
                85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
            165
```

<210> SEQ ID NO 39
<211> LENGTH: 500
<212> TYPE: DNA
<213> ORGANISM: Artificial Sequence
<220> FEATURE:
<223> OTHER INFORMATION: Gene Fusion
<220> FEATURE:
<221> NAME/KEY: CDS
<222> LOCATION: (1)..(498)

<400> SEQUENCE: 39

```
tgt gat ctg cct cag acc cac agc ctg ggt aat agg agg gcc ttg ata    48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac    96
Leu Leu Ala Gln Met Gly Arg Ile Ser Pro Phe Ser Cys Leu Lys Asp
            20                  25                  30 aga cat gac ttt gga ttc ccc cag gag gag ttt gat ggc aac cag ttc   144
Arg His Asp Phe Gly Phe Pro Gln Glu Glu Phe Asp Gly Asn Gln Phe
        35                  40                  45 cag aag gct caa gcc atc tct gtc ctc cat gag atg atc cag cag acc   192
Gln Lys Ala Gln Ala Ile Ser Val Leu His Glu Met Ile Gln Gln Thr
    50                  55                  60
```

```
                  50                  55                  60
ttc aat ctc ttc agc aca aag gac tca tct gct act tgg gaa cag agc      240
Phe Asn Leu Phe Ser Thr Lys Asp Ser Ser Ala Thr Trp Glu Gln Ser
 65                  70                  75                  80 ctc cta gac aaa ttc tcc act gaa ctc tac cag cag ctg aat gac ctc      288
Leu Leu Asp Lys Phe Ser Thr Glu Leu Tyr Gln Gln Leu Asn Asp Leu
                 85                  90                  95 gag gcc tgt gtg ata cag ggg gtg ggg gtg aca gag act ccc ctg atg      336
Glu Ala Cys Val Ile Gln Gly Val Gly Val Thr Glu Thr Pro Leu Met
            100                 105                 110 aag gag gac tcc att ctg gct gtg agg aaa tac ttc caa aga atc act      384
Lys Glu Asp Ser Ile Leu Ala Val Arg Lys Tyr Phe Gln Arg Ile Thr
        115                 120                 125 ctc tat ctg aaa gag aag aaa tac agc cct tgt gcc tgg gag gtt gtc      432
Leu Tyr Leu Lys Glu Lys Lys Tyr Ser Pro Cys Ala Trp Glu Val Val
    130                 135                 140 aga gca gaa atc atg aga tct ttt tct ttg tca aca aac ttg caa gaa      480
Arg Ala Glu Ile Met Arg Ser Phe Ser Leu Ser Thr Asn Leu Gln Glu
145                 150                 155                 160 agt tta aga agt aag gaa tg                                           500
Ser Leu Arg Ser Lys Glu
                165

<210> SEQ ID NO 40
<211> LENGTH: 166
<212> TYPE: PRT
<213> ORGANISM: Artificial Sequence
<220> FEATURE:
<223> OTHER INFORMATION: Gene Fusion

<400> SEQUENCE: 40

Cys Asp Leu Pro Gln Thr His Ser Leu Gly Asn Arg Arg Ala Leu Ile
  1               5                  10                  15

Leu Leu Ala Gln Met Gly Arg Ile Ser Pro Phe Ser Cys Leu Lys Asp
             20                  25                  30

Arg His Asp Phe Gly Phe Pro Gln Glu Glu Phe Asp Gly Asn Gln Phe
         35                  40                  45

Gln Lys Ala Gln Ala Ile Ser Val Leu His Glu Met Ile Gln Gln Thr
     50                  55                  60

Phe Asn Leu Phe Ser Thr Lys Asp Ser Ser Ala Thr Trp Glu Gln Ser
 65                  70                  75                  80

Leu Leu Asp Lys Phe Ser Thr Glu Leu Tyr Gln Gln Leu Asn Asp Leu
                 85                  90                  95

Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
    130                 135                 140

Arg Ala Glu Ile Met Arg Ser Phe Ser Leu Ser Thr Asn Leu Gln Glu
145                 150                 155                 160

Ser Leu Arg Ser Lys Glu
                165

<210> SEQ ID NO 41
<211> LENGTH: 500
<212> TYPE: DNA
<213> ORGANISM: Artificial Sequence
<220> FEATURE:
```

```
<223> OTHER INFORMATION: Gene Fusion
<220> FEATURE:
<221> NAME/KEY: CDS
<222> LOCATION: (1)..(498)

<400> SEQUENCE: 41 tgt gat ctg cct cag acc cac agc ctg ggt aat agg agg gcc ttg ata    48
Cys Asp Leu Pro Gln Thr His Ser Leu Gly Asn Arg Arg Ala Leu Ile
1               5                   10                  15 ctc ctg gca caa atg gga aga atc tct cct ttc tcc tgc ctg aag gac    96
Leu Leu Ala Gln Met Gly Arg Ile Ser Pro Phe Ser Cys Leu Lys Asp
            20                  25                  30 aga cat gac ttt gga ttc ccc cag gag gag ttt gat ggc aac cag ttc    144
Arg His Asp Phe Gly Phe Pro Gln Glu Glu Phe Asp Gly Asn Gln Phe
        35                  40                  45 cag aag gct caa gcc atc tct gtc ctc cat gag atg atc cag cag acc    192
Gln Lys Ala Gln Ala Ile Ser Val Leu His Glu Met Ile Gln Gln Thr
    50                  55                  60 ttc aat ctc ttc agc aca aag gac tca tct gct act tgg gaa cag agc    240
Phe Asn Leu Phe Ser Thr Lys Asp Ser Ser Ala Thr Trp Glu Gln Ser
65                  70                  75                  80 ctc cta gac aaa ttc tac act gaa ctc aac cag cag ctg aat gac ctc    288
Leu Leu Asp Lys Phe Tyr Thr Glu Leu Asn Gln Gln Leu Asn Asp Leu
                85                  90                  95 gag gcc tgt gtg ata cag ggg gtg ggg gtg aca gag act ccc ctg atg    336
Glu Ala Cys Val Ile Gln Gly Val Gly Val Thr Glu Thr Pro Leu Met
            100                 105                 110 aag gag gac tcc att ctg gct gtg agg aaa tac ttc caa aga atc act    384
Lys Glu Asp Ser Ile Leu Ala Val Arg Lys Tyr Phe Gln Arg Ile Thr
        115                 120                 125 ctc tat ctg aaa gag aag aaa tac agc cct tgt gcc tgg gag gtt gtc    432
Leu Tyr Leu Lys Glu Lys Lys Tyr Ser Pro Cys Ala Trp Glu Val Val
    130                 135                 140 aga gca gaa atc atg aga tct ttt tct ttg tca aca aac ttg caa gaa    480
Arg Ala Glu Ile Met Arg Ser Phe Ser Leu Ser Thr Asn Leu Gln Glu
145                 150                 155                 160 agt tta aga agt aag gaa tg                                         500
Ser Leu Arg Ser Lys Glu
                165

<210> SEQ ID NO 42
<211> LENGTH: 166
<212> TYPE: PRT
<213> ORGANISM: Artificial Sequence
<220> FEATURE:
<223> OTHER INFORMATION: Gene Fusion

<400> SEQUENCE: 42

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Asp Lys Phe Tyr Thr Glu Leu Asn Gln Gln Leu Asn Asp Leu
                85                  90                  95
```

-continued

```
Glu Ala Cys Val Ile Gln Gly Val Gly Val Thr Glu Thr Pro Leu Met
            100                 105                 110

Lys Glu Asp Ser Ile Leu Ala Val Arg Lys Tyr Phe Gln Arg Ile Thr
        115                 120                 125

Leu Tyr Leu Lys Glu Lys Lys Tyr Ser Pro Cys Ala Trp Glu Val Val
        130                 135                 140

Arg Ala Glu Ile Met Arg Ser Phe Ser Leu Ser Thr Asn Leu Gln Glu
145                 150                 155                 160

Ser Leu Arg Ser Lys Glu
                165
```

What is claimed is:

1. A purified hybrid interferon-α polypeptide, comprising a first amino acid sequence consisting of residues 1-75 of interferon-α21b, a second amino acid sequence consisting of residues 76-81 of interferon-α2c or residues 76-81 of interferon-α21b; a third amino acid sequence consisting of the sequence LDKFXTELXQQLND (SEQ ID NO: 43) or the sequence LEKFXTELXQQLND (SEQ ID NO: 44), wherein X is any amino acid residue; and a fourth amino acid sequence consisting of residues 96-166 of interferon-α2c; wherein the C-terminal residue of the first amino acid sequence is fused to the N-terminal residue of the second amino acid sequence; and the C-terminal residue of the second amino acid sequence is fused to the N-terminal residue of the third amino acid sequence; and the C-terminal residue of the third amino acid sequence is fused to the N-terminal residue of the fourth amino acid sequence; and wherein the hybrid interferon-α polypeptide has interferon-α protein biological activity.

2. The purified hybrid interferon-α polypeptide according to claim 1, wherein the second amino acid sequence consists of residues 76-81 of interferon-α2c.

3. The purified hybrid interferon-α polypeptide according to claim 1, wherein the second amino acid sequence consists of residues 76-81 of interferon-α21b.

4. The purified hybrid interferon-α polypeptide according to claim 1, wherein the third amino acid sequence consists of the sequence LDKFXTELXQQLND (SEQ ID NO: 43).

5. The purified hybrid interferonα polypeptide according to claim 1, wherein the third amino acid sequence consists of the sequence LEKFXTELXQQLND (SEQ ID NO: 44).

6. The hybrid interferon polypeptide according to claim 1, wherein the second amino acid sequence consists of residues 76-81 of interferon-α2c and the third amino acid sequence consists of the sequence LEKFXTELXQQLND (SEQ ID NO: 44).

7. The hybrid interferon-α polypeptide according to claim 6, comprising an amino acid sequence with a structure M-N-O-P, wherein M consists of amino acid residues 1-75 of interferon-α21b, N consists of amino acid residues 76 to 81 of interferon-α2c, O consists of amino acid residues 82 to 95 of interferon-α21b, and P consists of amino acid residues 96 to 166 of interferon-α2c.

8. The hybrid interferon-α polypeptide according to claim 1, wherein the second amino acid sequence consists of residues 76-81 of interferon-α2c and the third amino acid sequence consists of the sequence LDKFXTELXQQLND (SEQ ID NO: 43).

9. The hybrid interferon-α polypeptide according to claim 1, wherein the second amino acid sequence consists of residues wherein the second amino acid sequence consists of residues 76-81 of interferon-α21b and the third amino acid sequence consists of the sequence LDKFXTELXQQLND SEQ ID NO: 43).

10. The hybrid interferon-α polypeptide according to claim 1, comprising an amino acid sequence selected from the group consisting of an amino acid sequence as set forth in SEQ ID NOs: 9, 11, 30, 32, 36, 38, 40, and 42.

11. The hybrid interferon-α polypeptide according to claim 10, wherein the sequence is selected from the group consisting of an amino acid sequence as set forth in SEQ ID NOs: 9, 32, 36, and 38.

12. The hybrid interferon-α polypeptide according to claim 1, wherein the second amino acid sequence consists of amino acid residues 76-95 of interferon-α2c.

13. The hybrid interferon-α polypeptide according to claim 1, wherein the second amino acid sequence consists of amino acid residues 76-95 of interferon-α21b.

14. The hybrid interferon-α polypeptide according to claim 8, wherein the second amino acid sequence consists of residues wherein the second amino acid sequence consists of residues 76-81 of interferon-α21b and the third amino acid sequence consists of the sequence LEKFXTELXQQLND (SEQ ID NO: 44).

15. A nucleic acid molecule encoding a polypeptide according to claim 1.

16. A recombinant vector comprising the nucleic acid molecule according to claim 15.

17. A cell transformed with the recombinant vector according to claim 16.

18. A pharmaceutical composition comprising:
a pharmaceutically acceptable vehicle or carrier; and
at least one hybrid interferon-α polypeptide according to claim 1.

19. A nucleic acid molecule encoding a polypeptide according to claim 10.

20. A nucleic acid molecule according to claim 19, having a nucleic acid sequence as set forth in SEQ ID NO: 8, 10, 29, 31, 35, 37, 39, or 41.

21. A recombinant vector comprising the nucleic acid molecule according to claim 19.

22. A cell transformed with the recombinant vector according to claim 21.

23. A pharmaceutical composition comprising:
a pharmaceutically acceptable vehicle or carrier; and
at least one hybrid interferon-α polypeptide according to claim 10.

* * * * *

UNITED STATES PATENT AND TRADEMARK OFFICE
CERTIFICATE OF CORRECTION

PATENT NO. : 7,235,232 B2
APPLICATION NO. : 10/615723
DATED : June 26, 2007
INVENTOR(S) : Zoon et al.

It is certified that error appears in the above-identified patent and that said Letters Patent is hereby corrected as shown below:

Column 16, Line 23, "SDM1 as" should be --SDM1as--.

Column 16, Line 30, "SDM2 as" should be --SDM2as--.

Column 16, Line 36, "SDM3 as" should be --SDM3as--.

Column 16, Line 42, "SDM4 as" should be --SDM4as--.

Column 17, Line 35, "the manufactures" should be --the manufacturers--.

Column 17, Line 40, "IFNA-b 2" should be --IFNA2--.

Column 18, Lines 6-7, "purification of may" should be --purification may--.

Column 18, Line 25, "1997)" should be --1997).--.

Column 18, Line 63, "Bethesda Md." should be --Bethesda, MD.--.

Column 20, Line 2, "with or without with" should be --with or without--.

Column 20, Line 10, "preformed" should be --performed--.

Column 20, Line 17, "1982" should be --1992--.

Column 21, Line 1, "IFN-α" should be --IFN-αX--.

Column 22, Line 10, "interferon α21b" should be --interferon-α21b--.

Column 22, Line 13, "interferon-α 21b" should be -- interferon-α21b--.

Column 22, Line 14, "interferon-α 2c." should be --interferon-α2c--.

Column 23, Line 35, "polyakylene" should be --polyalkylene--.

Column 24, Table 1, Header, "(ng/ml)$^8$" should be --(ng/ml)$^a$--.

Column 24, Table 1, Column 1, "IFN-α21a" should be --IFN-α21b--.

UNITED STATES PATENT AND TRADEMARK OFFICE
CERTIFICATE OF CORRECTION

| | |
|---|---|
| PATENT NO. | : 7,235,232 B2 |
| APPLICATION NO. | : 10/615723 |
| DATED | : June 26, 2007 |
| INVENTOR(S) | : Zoon et al. |

It is certified that error appears in the above-identified patent and that said Letters Patent is hereby corrected as shown below:

Column 24, Table 1, Legend, "$^{128}$I-IFN-α2b" should be --$^{125}$I-IFN- α2b--.

Column 25, Table 1, Column 2, "NID" should be --N/D--.

In the Sequence Listing:
SEQ ID NOs: 43 and 44
Sequence Listing:

Col. 59 should read

<210> SEQ ID NO 43
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 43

Leu Asp Lys Phe Xaa Thr Glu Leu Xaa Gln Gln Leu Asn Asp
1               5                   10

UNITED STATES PATENT AND TRADEMARK OFFICE
CERTIFICATE OF CORRECTION

PATENT NO.       : 7,235,232 B2
APPLICATION NO.  : 10/615723
DATED            : June 26, 2007
INVENTOR(S)      : Zoon et al.

It is certified that error appears in the above-identified patent and that said Letters Patent is hereby corrected as shown below:

Col. 59 should read

```
<210> SEQ ID NO 44
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 44

Leu Glu Lys Phe Xaa Thr Glu Leu Xaa Gln Gln Leu Asn Asp
1               5                   10
```

Column 59, Line 44, "interferonα" should be --interferon-α--.

Column 59, Line 64 to Column 60, Line 19, "wherein the second amino acid sequence consists of residues wherein the second amino acid sequence consists of residues 76-81" should be --wherein the second amino acid sequence consists of residues 76-81--.

UNITED STATES PATENT AND TRADEMARK OFFICE
CERTIFICATE OF CORRECTION

PATENT NO.        : 7,235,232 B2
APPLICATION NO.   : 10/615723
DATED             : June 26, 2007
INVENTOR(S)       : Zoon et al.

It is certified that error appears in the above-identified patent and that said Letters Patent is hereby corrected as shown below:

Column 60, Line 37, "wherein the second amino acid sequence consists of residues wherein the second amino acid sequence consists of 76-81" should be --wherein the second amino acid sequence consists of 76-81--.

Signed and Sealed this

Twenty-ninth Day of December, 2009

David J. Kappos
*Director of the United States Patent and Trademark Office*